(12) United States Patent
Gerdes et al.

(10) Patent No.: US 7,316,913 B2
(45) Date of Patent: Jan. 8, 2008

(54) METHODS AND MEANS FOR INFLUENCING INTRACELLULAR COMMUNICATION AND INTRACELLULAR ORGANELLE TRANSPORT

(75) Inventors: Hans-Hermann Gerdes, Heidelberg (DE); Amin Rustom, Heidelberg (DE)

(73) Assignee: Stiftelsen Universitetsforskning Bergen, Bergen (NO)

( * ) Notice: Subject to any disclaimer, the term of this patent is extended or adjusted under 35 U.S.C. 154(b) by 0 days.

(21) Appl. No.: 10/496,126

(22) PCT Filed: Nov. 22, 2002

(86) PCT No.: PCT/EP02/13140

§ 371 (c)(1),
(2), (4) Date: Jul. 16, 2004

(87) PCT Pub. No.: WO03/044524

PCT Pub. Date: May 30, 2003

(65) Prior Publication Data

US 2005/0064534 A1     Mar. 24, 2005

(30) Foreign Application Priority Data

Nov. 23, 2001 (DE) ............................... 101 57 475

(51) Int. Cl.
*C12Q 1/02* (2006.01)
(52) U.S. Cl. .................................................. 435/29 C
(58) Field of Classification Search ..................... None
See application file for complete search history.

(56) References Cited

FOREIGN PATENT DOCUMENTS

WO    WO 98/02186 A1    1/1998

OTHER PUBLICATIONS

Woodruff et al, "Intercellular Bridges between Epithelial Cells in the Drosophila Ovarian Follicle: A Possible Aid to Localized Signaling," (Dev. Biol.), 1998, vol. 200, p. 82-91.*
Rustom et al, "Analysis of Fast Dynamic Processes in Living Cells: High-Resolution and High-Speed Dual-Color Imaging Combined with Autmoated Image Analysis," (BioTechniques), 2000, vol. 28, p. 722-726, 728, 730.*
Yang et al, "Dual color microscopic imagery of cells expressing the green fluorescent protein and a red-shifted variant," (Gene), 1996, vol. 173, p. 19-23.*
Ramirez-Weber et al, "Cytonemes: Cellular Processes that Project to the Principal SIgnaling Center in Drosophila Imaginal Discs," (Cell), 1999, vol. 97, p. 599-607.*
Rudolf et al, "Dynamics of Immature Secretory Granules: Role of Cytoskeletal Elements during Transport, Cortical Restriction, and F-Actin-dependent Tethering," (Molec. Biol.), 2001, vol. 12, p. 1353-1365.*
Elliott G et al., Cell, Cell vol. 88, pp. 223-233, 1997.
Nathalie et al., Journal of Neuroscience Methods, vol. 73, No. 2, 1997, pp. 169-176.

* cited by examiner

*Primary Examiner*—Jon Weber
*Assistant Examiner*—Amanda P. Wood
(74) *Attorney, Agent, or Firm*—Birch, Stewart, Kolasch & Birch, LLP

(57) ABSTRACT

The invention relates to a method for the investigation of intercellular communication and intercellular transport, wherein after singularisation cells are investigated for membrane tubes which contain F-actin and myosin, have a diameter of 50 to 400 nm, as a rule are up to 50 micrometers long or in same cases longer, and which span between the cells. The invention further relates to a method wherein the organelle transport between the cells is investigated.

14 Claims, 21 Drawing Sheets

METHODS AND MEANS FOR INFLUENCING INTRACELLULAR COMMUNICATION AND INTRACELLULAR ORGANELLE TRANSPORT

This application is the U.S. National Phase of International Application PCT/EP02/13140 filed Nov. 22, 2002, which claims priority to DE Patent Application No. 10157475.4, filed Nov. 23, 2001.

FIELD OF THE INVENTION

The invention relates to pharmaceutical and physical means for influencing cell interactions, intercellular transport and intercellular communication, and method and means for the investigation thereof.

BACKGROUND OF THE INVENTION

The cells in multicellular organisms and assemblies effect exchanges only through predetermined paths. Communication over short paths is effected so far as known via gap junctions, plasmodesmata or synaptic connections (chemical synapses).

Gap Junctions have protein pores of connexin proteins having a pore size of about 1.5 nanometres. Gap Junctions do not provide a membrane continuum between the cells, but connect neighbouring cells over a distance of 2 to 4 nanometers through the passing on of electrical signals and the passive exchange of small molecules having a molecular weight up to 1000 Dalton, in exceptional cases up to 5000 Dalton. The signal flow is regulated by means of the calcium concentration and/or the applied potential, for which reason gap junctions are also characterized as "electrical synapses". A transport of membrane vesicles is not described. Gap junctions are found in animal and fungus cells. In plants, only connexin-like proteins have been identified to date.

Plasmodesmata are membrane-surrounded cytoplasma channels. They connect neighbouring plant cells via pores in the cell walls having a diameter of ca. 60 nanometers. This leads to a membrane continuum between the connected cells. The endoplasmic reticuli of connected cells can also extend over plasmodesmata. Plasmodesmata are transparent for small molecules, nutrients, ribonucleic protein complexes, ions and fluorescent dyes. The size rejection limit of plasmodesmata is at circa 1 to 4 kilodalton, but also a few much larger viruses use plasmodesmata as a path for infection. Vesicle transport via plasmodesmata is, however, not known to date.

Synaptic connections are cell continuations (axons) which are connected at their end via a synapse with the surface of another cell. Synapse and target cell are separated by a synaptic gap ca. 20 nanometers wide. The diameter of an axon is ca. 0.3 to 1.3 micrometer. Axons contain microtubules and make possible a bi-directional vesicle transport up to the synapse. Information exchange is effected through the excretion of signal substances at the synapse. These substances diffuse over the synaptic gap to the target cell where through binding to specific receptors they lead to signal transmission. Synaptic connections are characteristic for the central and peripheral nervous system.

Communication or the exchange of information over longer paths is effected, so far as known, via cytonemes, argosomes and via the excretion of messenger substances via the endocrine system.

Cytonemes are fine cell extensions, ca. 200 nanometers thick, which mostly end free in extracellular space, but sometimes also stand in contact with other cells. The extensions contain actin, but no microtubules. At the present time it is not known how cytonemes contribute to intercellular communication. Cytonemes have been detected in insects (Drosophilia, imaginal disk cells), Calpodes, Rhodnius and sea urchin embryos. An occurrence in mammal cells has not to date been described.

Argosomes are membrane vesicles occurring intracellular and extracellular which can transport signal substances from cell to cell. The mechanism of intercellular transport of argosomes has not yet been determined. It is postulated that argosomes are transported via endocytotic and exocytotic mechanisms. Argosomes have to date only been found ii Drosophila embryos.

Endocrine communication between cells distinguishes itself through the excretion of signal substances such as e.g. hormones into the bloodstream, followed by a receptor-mediated effect on the target cells. Endocrine communication is a general principle in organisms.

It is the object of the invention to reveal further forms of interaction, transport and communication between cells. It is in particular the object of the invention to make available pharmaceutical and physical means which can influence communication between cells and intercellular transport. Further it is an object of the invention to make available means and methods for the investigation of the new forms of cell communication and intercellular transport.

SUMMARY OF THE INVENTION

This object is achieved by means of a method of investigating intercellular communication and intercellular transport in which cells, after singularisation, are investigated for membrane tubes which contain F-Actin and myosin, which have a diameter of 50 to 400 nm, which as a rule are up to 50 micrometers or in individual cases longer, and which extend between the cells.

A second aspect of the invention relates to the investigation of organelle transport between the cells via such membrane tubes, for example by means of the steps: (i) addition of one or more substances to a first number of cells, the substance being so selected that it is endocyted by the cells of the first number within a first period of time; (ii) mixing of the first number of cells after washing with a second number of cells, so that between the cells of the first and second numbers intercellular membrane tubes form within a second period of time, and (iii) determination of the number of the cells of the second number of cells which contain the one or more endocyted substances. In another embodiment, in step (i) the first number of cells is treated with a first endocytable substance and the second number of cells is treated with a second endocytable substance, wherein the first and second substances are different. The endocytable substances may be selected from one or more dyes, fluorescent dyes, Dil, DiO, LYSOTRACKER™, radioactive marker substances, luminescent dyes, fluorescing or luminescing proteins and peptides, proteins or peptides which are coupled with a marker substance. These investigations can alternatively also be so effected that in step (i) a endocytable substance is not tracked, but that one first achieves a constitutive or transient expression of a detection substance in the organelles. Step (iii) may be effected by means of FACS.

In a third aspect of the present invention the investigation of the organelle transport is effected in the presence or under the effect of a test medium. The test medium may be a chemical compound or a suspected pharmaceutically effective substance, preferably a medicament or therapeutic agent. The test medium may also be a physical device, preferably a physical therapeutic device.

In a further aspect of the invention, the investigation is effected with a microscope system which permits the observation of various microscopic planes in the Z-axis. The microscope system includes preferably a microscope, a Z-stepper and an associated controller.

A further aspect of the invention relates to the employment of the above-mentioned method and of the devices for serial investigation of suspected medicaments and effective substances, in particular for the serial investigation of suspected effective substances and effective media for the treatment of tumours, high blood pressure, of viral, bacterial or parasitic infectious diseases, diseases of the metabolism, diseases of the nervous system, the psyche and the mind, and of the cholesterol level. A further employment of the method in accordance with the invention lies in the investigation of effective substances in gene therapy, for cell targeting and in pharmacology. The invention also relates to pharmaceutical compositions which contain the so determined effective substances and also therapeutic procedures on the basis of the effective means for influencing intercellular communication and intercellular organelle transport.

Further advantages, objects and features of the invention are provided in the examples and the accompanying Figures.

DESCRIPTION OF THE DRAWINGS

There is Shown:

FIG. 1a—high resolution, three-dimensional videomicroscopy recording of living PC12 cells about 24 hours after cell passage and colouring with WGA, and a TNT (image center) which bridges two PC12 cells over a very long distance (bar:15 micrometers);

FIG. 1b—image in accordance with FIG. 1a, which shows a plurality of TNTs, which starting from one cell extend to various cells (bar:15 micrometers);

FIG. 1c—image according to FIG. 1a of a branched TNT (see arrow);

FIG. 1d—a computer generated (x-z) individual section of a TNT, which stretches between two PC12 cells without contact with the substrate, FIG. 1e—an (x-y) individual section from a three-dimensional reconstruction of a videomicroscopic multi-colour fluorescence image of fixed PC12 cells, connected via TNTs, after immune staining with an anti-tubulin antibodies (green), FITC phalloidin actin stain (red) and DAPI nucleus staining (blue, Molecular Probes D-1306)—the occurrence of tubulin is restricted to the cell bodies, whilst the occurrence of the actin extends over the TNTs (arrow); the insert shows the corresponding (x-z) individual section through the arrow marked TNT (bar:15 micrometers);

FIG. 1f—a raster electron microscope image of TNTs: PC12 cells were fixed for 30 minutes with 2.5% glutaraldehyde in 0.1 M phosphate buffer (pH 7.4), supplemented with 1% saccharose, and prepared for microscopy in the usual manner; f) TNT between two cells; f1) f2) and f3) are enlarged details of the boxed regions of (f) and show the base parts and the middle region of the TNT with a diameter of ca. 50 nm—the base parts clearly build a membrane continuum with the plasma membranes of the connected cells; (bar: large image 15 micrometers, small images 200 nm).

FIG. 1g—transmission electron microscopic image of a TNT having a diameter of 50 nm, which connects two fixed PC12 cells. The boxes show enlargements of the TNT bases. Star=secretory granulum (bar: large image 10 micrometers, small images 200 nm);

FIG. 11*a*—a graphical illustration of the temporal appearance of TNTs in the case of PC12 cells in the absence of latrunculin B. Abcissa: measured time point after cell passage in hours (h); ordinate: number of de novo formed TNTS, in randomly selected regions of the cell culture vessel, determined by means of plasma membrane staining of the cells with WGA and three-dimensional fluorescence microscopy analysis.

FIG. 11b—a graphical illustration of the temporal appearance of TNTs in the case of PC12 cells in the presence of 5 micromolar latrunculin B. Abcissa: measured time point after cell passage in hours (h) in the presence (+) and absence (−) of latrunculin B after cell passage; ordinate: number of de novo formed TNTs in 10 randomly selected regions of the cell culture vessel, determined by means of plasma membrane staining of the cells with WGA and three dimensional fluorescent microscopy analysis.

FIG. 12a—fluorescence microscopy image of PC12 cells ca. 1 hour after cell passage and staining with WGA, 20 minutes fixing in 4% paraformaldehyde/4% sucrose, 3 minutes treatment with 0.2% TRITON™ X-100 and nucleus staining with Dapi—left images in (a): the 14 hour long treatment of the cells before passage with 2.5 mM thymidin in the cell culture medium blocked the cells in the G1/S phase of the cell cycle and prevented a division of the cells; right images in (a): in non-treated PC12 cells (controls) there can be observed in the nucleus staining mitosis stadia (arrows). Despite the absence of mitosis stadia the thymidin treated PC12 cells form TNTs (arrow tips), (bar: 20 micrometer);

FIG. 12b—a graphical illustration and quantitative analysis of the results of FIG. 12a—in comparison with the controls the number of mitosis stadia was reduced by means of thymidin treatments to 20%, but the TNT formation was retained at 86.5% (the slight reduction is probably the result of the reduced number of cells due to the cell division block); the TNTs are thus not a phenomenon of cell division or the result of an incompletely developed cytokinesis;

FIG. 17a—a fluorescent microscopy image of PC12 cells which were analysed ca. 24 hours after transfection with VP22-GFP. A strongly fluorescing TNT connection (arrow) between a strongly and a weakly positive cell (stars) is conspicuous. Within this connection there appear strongly fluorescing vesicular structures (arrow tips), which in the course of the observation changed their position.

FIG. 17b—transmission microscopy image corresponding to FIG. 17a. The stars mark the same cells as in FIG. 17a.

FIG. 17c—a superposition of FIG. 17a (red) and 17b (blue).

FIG. 17d—a fluorescence microscopy analysis of PC12 cells 48 hours after transfection with VSVG-ECFP (Rustom, A., Bajohrs, M., Kaether, C., Kellner, P., Toomre, D., Corbeil, D., Gerdes, H.-H.: *Selective delivery of secretory cargo in Golgi-derived carriers of non-epithelial cells*, in Traffic 2002, 3: 279-288) and plated onto LABTEK™ cell culture bowls. Apart from the VSVG-ECFP expressing cells (arrow tips) two further cells (stars) connected with these via TNTs show a plasma membrane staining. One notes that also the TNTs between the cells are strongly stained with VSVG-ECFP (arrows). From this it follows that viral VSVG-ECFP is transferred between cells via the TNT connection, (bar: 20 micrometer);

FIGS. 17e, f—transfer of HLA-A2-EGFP, a component of the MHC I-complex. Image in accordance with FIGS. 3f-i2, but the cells of population 1 were transfected with HLA-A2-EGFP. One notes that HLA-A2-EGFP could be selectively detected in cells of population 2 connected via TNTs (arrow tips), i.e. was transferred between TNT connected cells.

DETAILED DESCRIPTION OF THE INVENTION AND ITS PERFORMANCE

Figure 1:
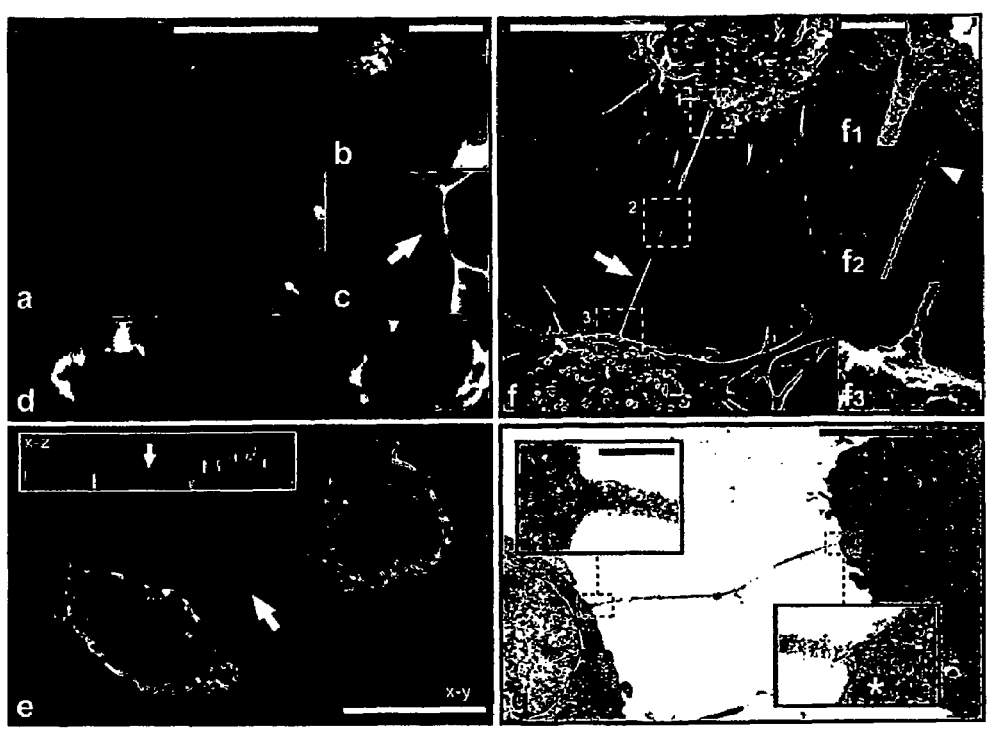
Figure 13:
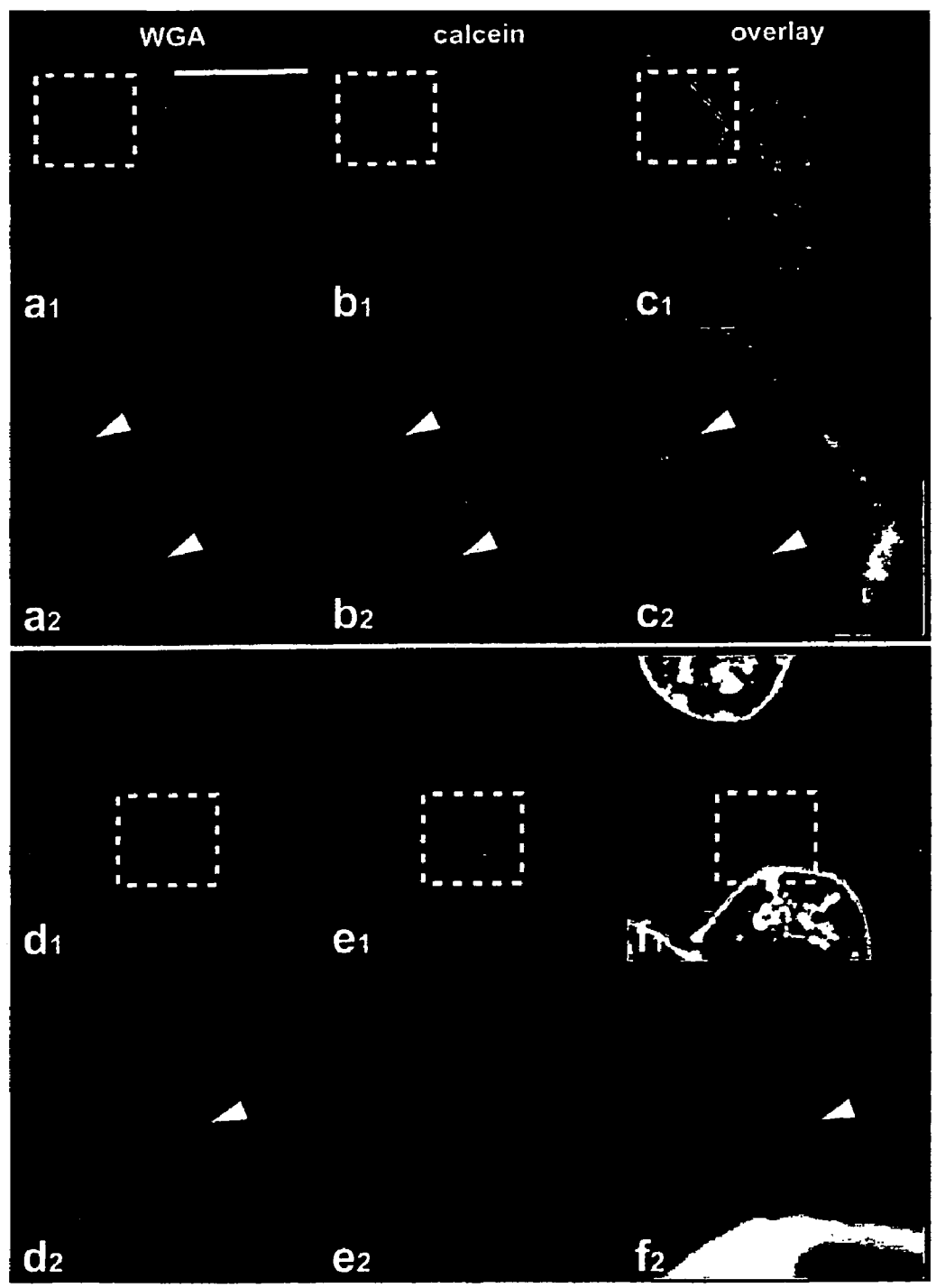
FIG. 13—calcein penetrates efficiently into filopodia but not into TNTs. 24 hours after plating, PC12 cells were stained with WGA (left column, red) and calcein AM (middle column, green, Molecular Probes C-3099, 1.3000) and then analysed by means of confocal fluorescence microscopy (the right column shows the overlay). The analysis of filopodia in optical (x-y) individual sections at the cell floor (a1-c2), where these structures are present in numbers, shows that calcein also efficiently stains filopodia. For the box regions in a1, b1, c1 there are shown in each case enlargements (a2, b2, c2) in which arrow tips mark the filopodia stained with calcein. In the analysis of TNTs (d1-f2) optical (x-y) individual sections through the cell middle, where the structures are typically localized, show that calcein does not penetrate into these. For the boxed regions in d1, e1, f1 enlargements are shown in each case (d2, e2, f2) in which arrow tips mark the TNT spanned between the cells, (bar: 15 micrometers)

In the investigation of protein secretion in a neuroendocrinic cell line there were observed, in the three-dimensional videomicroscopic investigation of the cell culture, tube-like transport channels which bridge neighbouring cells over in part very great distances of a number of cell diameters (FIG. 1). The tube strands were observed by chance after staining of the plasma membrane with fluorescence marked wheat germ agglutin (WGA) during the setting of the focal plane on the fluorescence videomicroscope (FIGS. 1a-c). The tubes are substantially straight and freely spanned between the cells, as if they stood under tension, and are mostly not in contact with the substrate (FIG. 1d). Their architecture differs from all previously known cells extensions. The tubes are as a rule up to 50 micrometers long and have a mean diameter of about 200 nanometres, which however in some cases can be up to 400 nm and more. Therefore, in the following, they will be called transport nanotubes or briefly, TNTs. Morphologically very similar structures, which were more than one millimetre long, were observed after a modified staining method (see FIG. 19). The TNTs are very sensitive with regard to electromagnetic waves such as light (FIG. 9), mechanical action (sound waves) and chemical fixing. However, no sensitivity of the TNTs with respect to trypsin/EDTA treatment was found (FIG. 10), a procedure which destroys a protein-mediated cell-cell adhesion. The immunohistochemical analysis shows that the TNTs contain filamentary actin (F-actin) but no microtubules (FIG. 1e, FIGS. 6d1-d3); similarly to cytonemes of drosophila imaginal disc cells (Ramirez-Weber F. A. et al., *Cytonemes: cellular processes that project to the principal signaling center in Drosophila imaginal discs*. Cell 97, 599-607 (1999)). Whereas for cytonemes a directed diffusion of signal substances, e.g. of morphogenes, has been postulated, with the exception of actin (FIGS. 3j-m2) we could not determine that in TNTs for example cytoplasmatic expressed recombinant proteins (for example EYFP, FIG. 7) or small dye molecules (for example calcein, FIGS. 13d-f2) were carried. The small inner diameter of the TNTs probably hinders a passive exchange of soluble molecules. This probably applies also for ions of the cytoplasma. In contrast, via TNTs components of the cell plasma membrane could be exchanged between the cells. Thus, we could show on fixed and living cells that farnesylated EGFP, a very specific plasma membrane marker (FIG. 8), is selectively exchanged between cells connected via TNTs (FIGS. 3n-q2, 4a-c). From this it follows that the plasma membranes of the corresponding cells represent a continuum.

Figure 16:
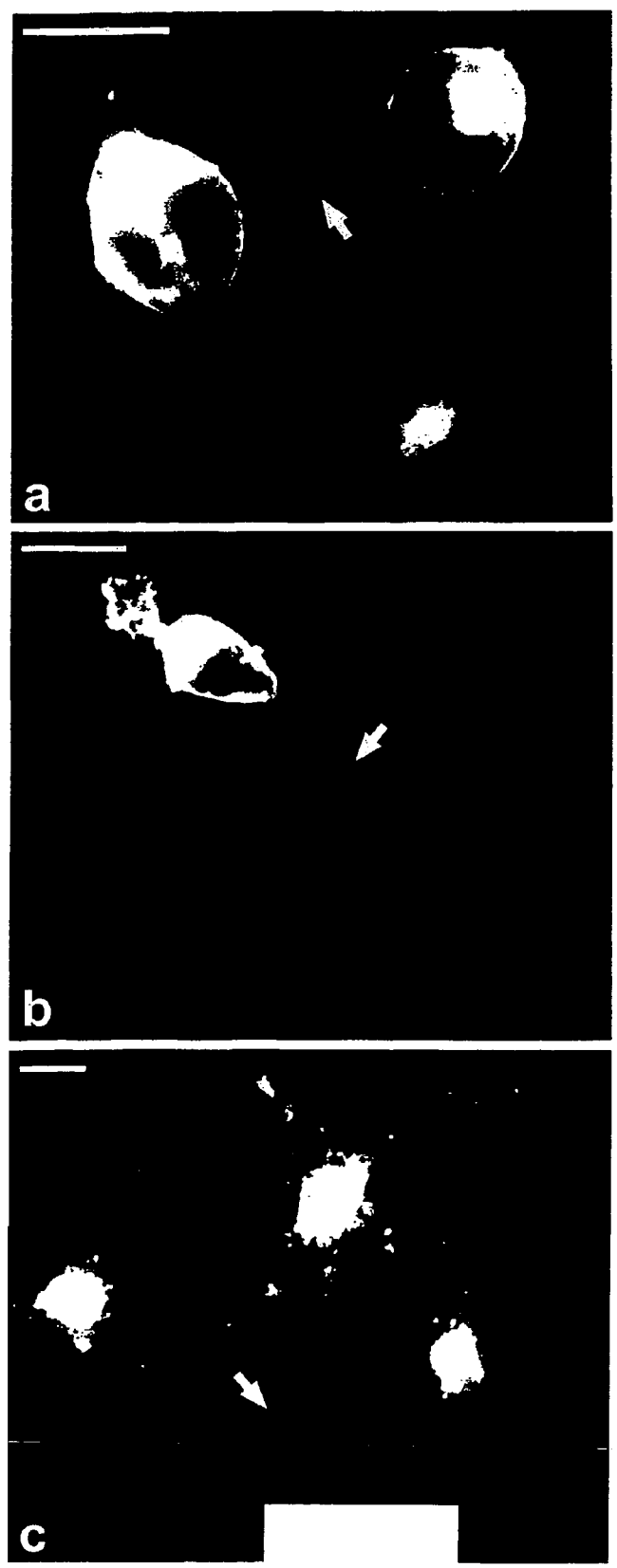
FIG. 16—an (x-y) individual section plane of a three-dimensional fluorescence videomicroscopy image. There are shown non-neuroendocrinic HEK-293 cells (a, ATCC CRL 1573—human embryonic kidney cells), medulla primary cultures of the rat (b, for the isolation of singularised cells the suprarenal medulla of P10 rats was subject to a collagenase (0.1%) and repeated trypsin treatments (0.125%); the singularised cells were then plated onto polyornithin/laminin coated LABTEK™ cell culture bowls and cultivated for four days) and hippocampural primary cultures (c, prepared in accordance with standard methods (Banker, G. Goslin, K. in *Cultering Nerve Cells*, eds. Banker G & Goslin K, MIT Press, Cambridge Mass., 1991) after staining with WGA. The TNTs (arrows) found in the cultures do not touch the substrate and span die shortest path between the respective cells (bar: 20 micrometers).

Further, we have found that in TNTs a prominent transport of membrane vesicles from one cell to the other takes place. By means of the new method we could observe under a light microscope that, in the TNTs spanned between the cells, vesicles are transported unidirectionally with a speed of 25.9±7.9 nanometres per second (n=6) (FIGS. 2g, h). Since TNTs could also be detected in the case of cultivated kidney epithelia cells (vero cells) human embryonal kidney cells (HEK, FIG. 16a) and also in primary cultures of medulla (FIG. 16b) and hippocampus tissue (FIG. 16) they are a general transport communication and interaction principle between cells. The intercellular transport of membrane structures between cell individuals via nanotubes was not known to date. Further the cell-cell communication based upon organelle transport represents a new biological functional principle which is of decisive significance for the development and maintenance of multicellular organisms. From this there are provided economically employable methods e.g. for medical diagnosis and therapy.

Figure 9:
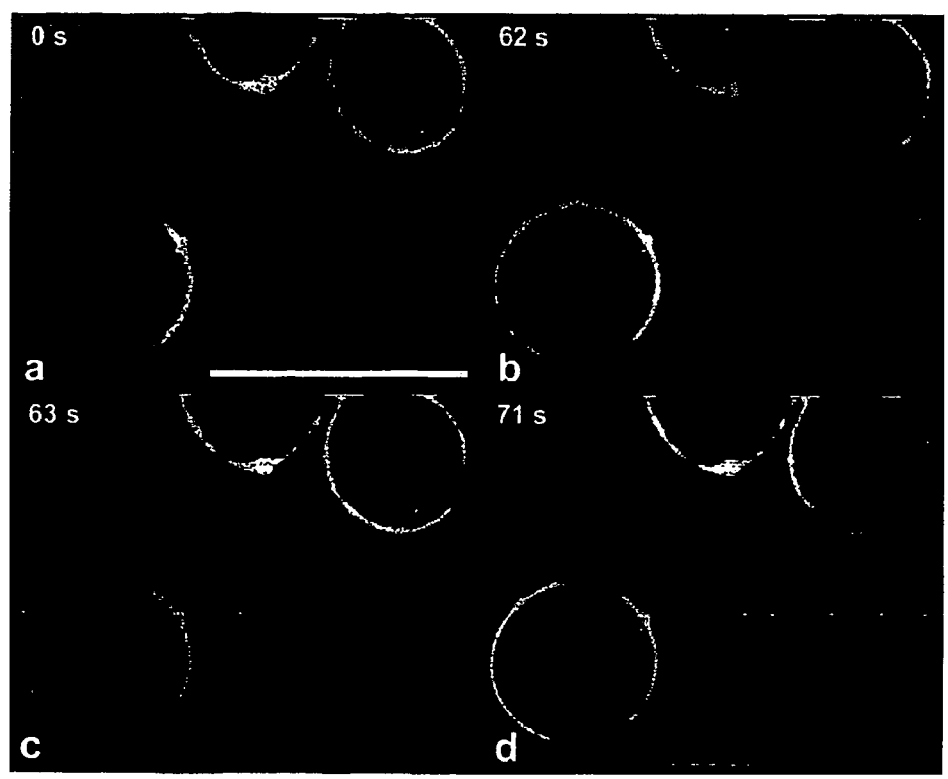
FIGS. 9*a-d*—four video microscopy images in accordance with FIG. 1*a* of a TNT over an observation period of ca. 70 seconds, in which the connection (a) is initially set into oscillation by the incident light of wavelength 565 nm (b), tears (c), and within seconds winds up at its free end like a torn elastic band (d). The time points of the images are indicated in seconds (s), (bar: 50 micrometers)
Figure 17:
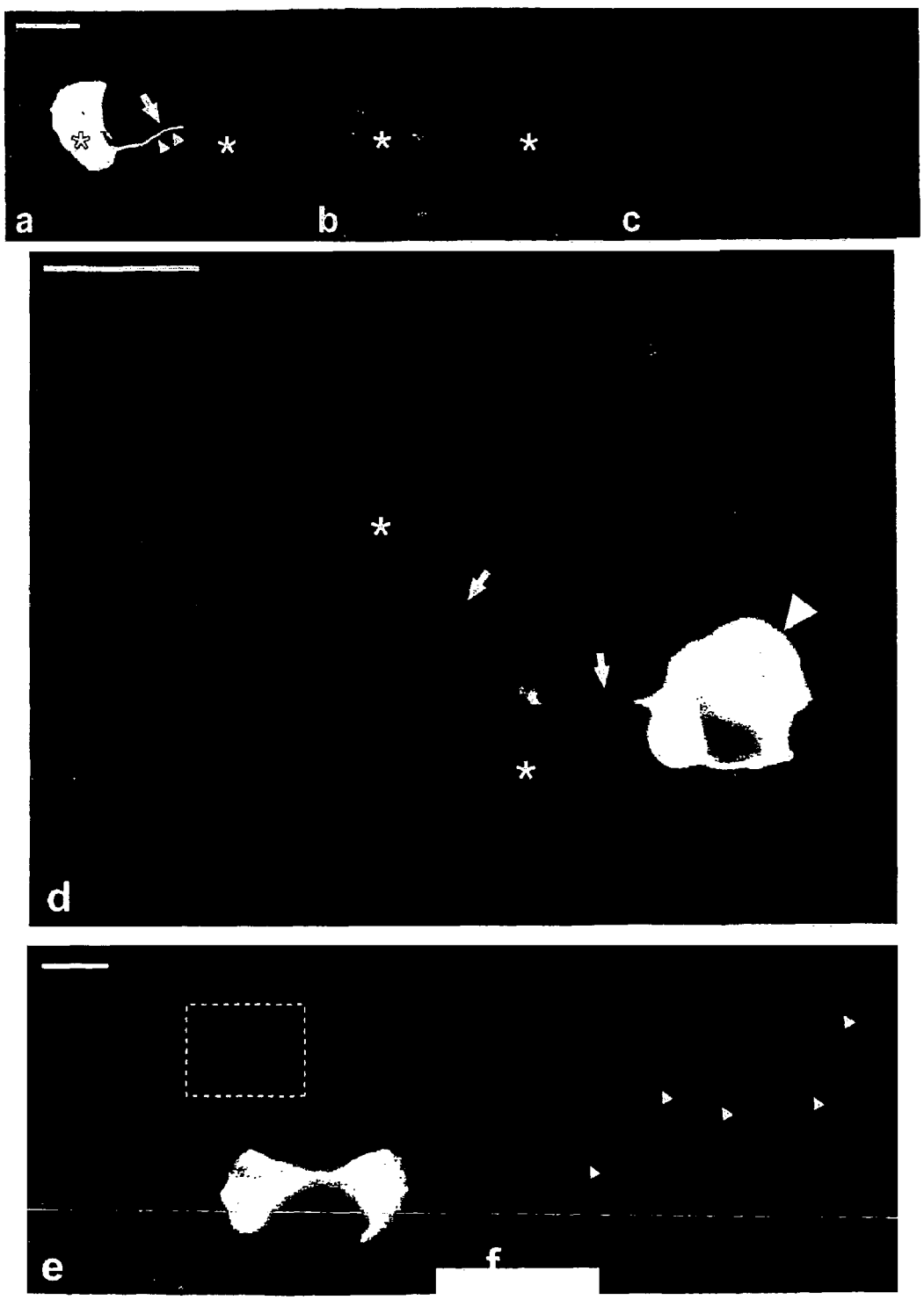

The highly sensitive TNTs, which were detected in dissociated cell cultures, probably also exist under physiological conditions in the tissue assembly. It is probable that they are there very similar in their structural and functional characteristics, but due to the local conditions have a different architecture. An altered architecture of TNTs (not stretched and following the cell contours) already showed itself in confluent assemblies of cultivated cells (see FIG. 17). To date, TNTs were not recognised or observed as such because first they are very sensitive and in cell cultures are as a rule destroyed due to the standard microscopy procedure, for example through the mechanical energy of the washing steps, chemical fixing methods or merely through the energy of the incident light (c.f. FIG. 9). Second, because with non-optimal cell culture conditions and unsuitable cell densities the number of TNTs stretched free between cells tends towards zero. Third, because the TNTs stretched between the cells lie in a plane of the cells which is unsuitable for most other microscopic studies and thus neglected. Fourth, because TNTs often develop not horizontally but with an inclination to the cell culture vessel, as a result of which they are not visible in one microscopy plane from beginning to end, i.e. can only be detected via a three-dimensional analysis.

Many pathogens depend in their multiplication and propagation cycle on intercellular transfer between cells. In a very many cases, the exact mechanisms of this transfer have not yet been explained. Thus, for example, the viral HSV1 tegument protein VP22 is exchanged extremely efficiently between cells (Wybranietz, W. A. et al. Enhanced suicide gene effect by adenoviral transduction of a VP22-cytosine deaminase (CD) fusion gene. *Gene Therapy* 8, 1654-1664 (2001)). Also proteins attached to VP22 are subject of this exchange, which makes VP22 an important tool for gene therapy methods ((Wybranietz, W. A. et al. Enhanced suicide gene effect by adenoviral transduction of a VP22-cytosine deaminase (CD) fusion gene. *Gene Therapy* 8, 1654-1664 (2001)). It is, however, to date unexplained how VP22 or VP22 fusion proteins get from one to the other cell. We assume that the TNTs described here can be used by pathogens as a route for infection. Our assumption is supported by experiments in which we were able to show that the viral protein VP22 (FIGS. 17*a-c*) and VSVG (FIG. 17*d*) are localised in TNTs, are there vesicularly transported and are transferred between the connected cells. Further evidence is the observation of others that VP22 can interact with actin and that the intercellular exchange of this protein can be prevented by means of destruction of the filamentary actin by cytochalasin D (Elliot, G. & O'Hare, P. Intercellular trafficking and protein delivery by a herpesvirus structural protein. *Cell* 88, 223-233 (1997)). In summary, TNTs and the influencing thereof are thus an important point of action e.g. for the improvement or creation of new gene therapeutic methods and the influencing and suppression of infectious diseases.

Figure 5:
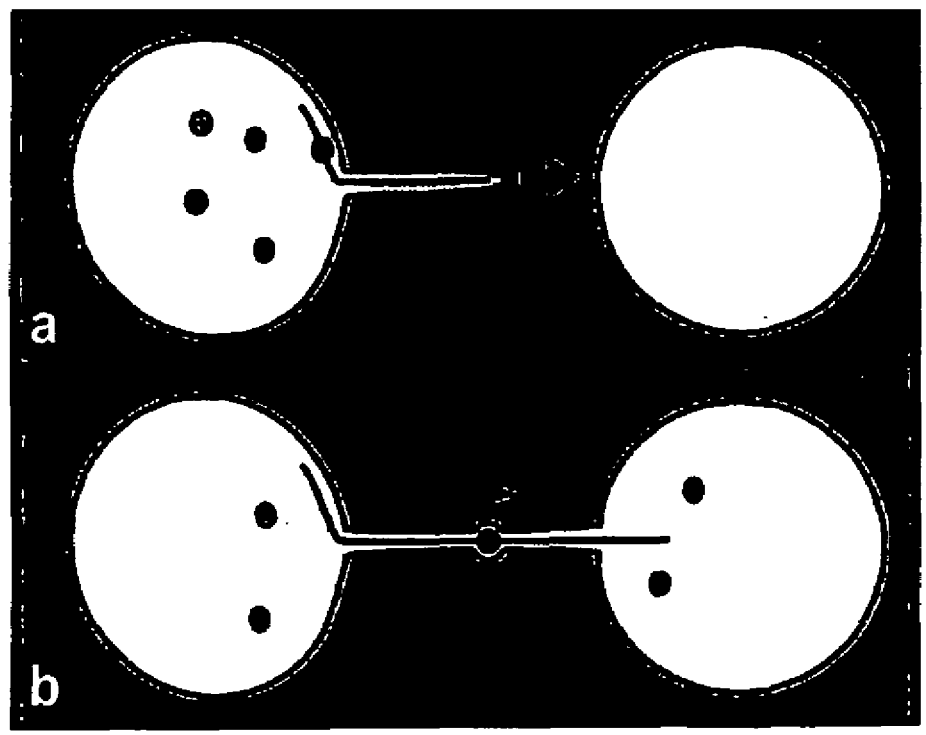
FIG. 5—sketched illustration of the TNT concept with indication of the individual results. One cell forms, in dependence upon actin, an extension (a) in the direction of a target cell. After fusion of the extension with the membrane of the target cell and formation of a membrane continuum between both cells (b), i.e. formation of a TNTs, organelles can be unidirectionally transferred between the cells. Red, actin: green, organelle.
Figure 18:
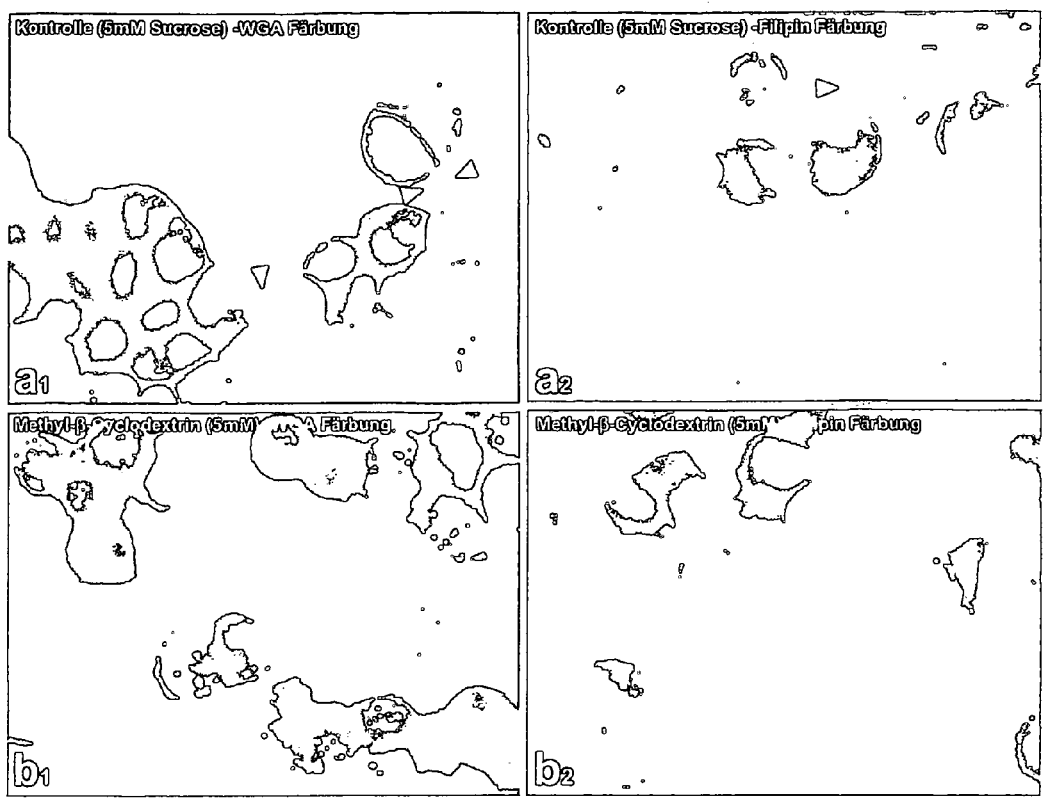
FIG. 18—the effect of cholesterol on the stability of TNTs. Two hours after passage of PC12 cells, the cell culture medium was exchanged for DMEM with 5, 8 or 10 millimolar saccharose (controls) or DMEM with 5, 8 or 10 mM methyl-β-cyclodextrin and the cells incubated for half an hour at 30° C. and 10% $CO_2$. After the addition of WGA a three-dimensional analysis of 10 randomly selected microscopic fields was carried out (Olympus IX70, 100× objective, TILLIVISION™ System, Piezo-z-stepper, in each case 40 sections) and the number of TNTs determined. (a1, b1) show representative image planes of the three-dimensional analysis for the 5 millimolar methyl-β-cyclodextrin conditions in which TNTs are marked with arrow tips. Quantifications yielded a strong reduction of the TNT number with increasing methyl-β-cyclodextrin concentration; 40% reduction at 5 millimolar methyl-β-cyclodextrin; 93% reduction at 8 millimolar methyl-β-cyclodextrin; 100% at 10 millimolar methyl-β-cyclodextrin (c1). In order to demonstrate the effect of methyl-β-cyclodextrin for reducing the cellular cholesterol content, a filipin staining (Sigma, F-765) was carried out (a2, b2). For this purpose, the methyl-β-cyclodextrin or saccharose containing DMEM of the analysed cell was exchanged with DMEM having 20 microgramm per millilitre filipin and 15 minutes later the intensity of the fluorescence staining analysed in vivo with a FITC/TRITC/DAPI filter set (Chroma, Brattleboro). In detail, after excitation at 400 nm four randomly selected microscopic fields were imaged and the mean grey scale values determined. The valuation of the treatment with 5 millimolar methyl-β-cyclodextrin yield the reduction of the cellular cholesterol content by 20% (c2)
Figure 18:
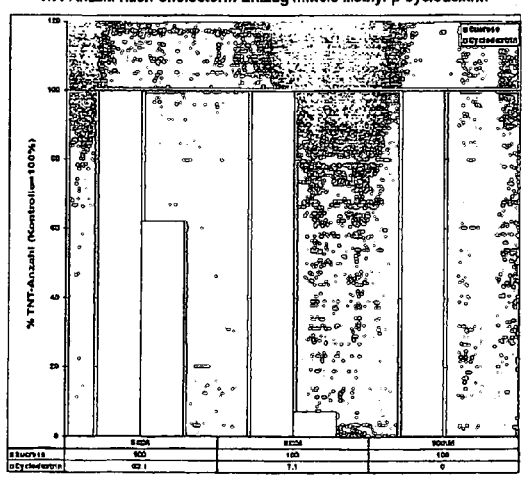
Figure 18:
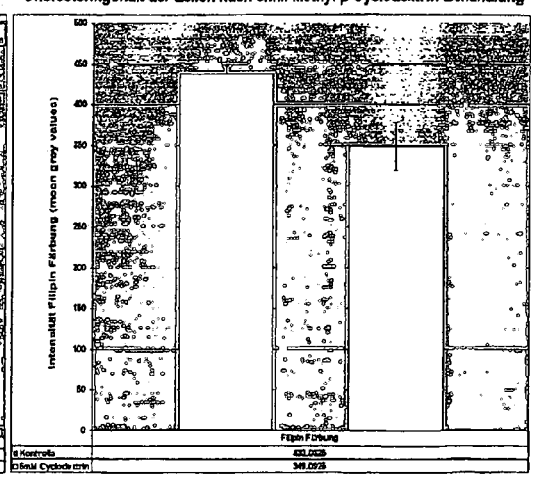

The newly discovered cell-cell connections can, due to their thread-like nature and lability, being influenced in may forms. (1) by means of sound, vibration, heat or hydromechanical energy forms and also (2) by light and other electromagnetic waves (cf. FIG. 9). Further, complex pathological body functions such as high blood pressure can be related via the TNT concept (FIG. 5) with subtle environmental influences such as electromagnetic radiation, noise and so on with an objective cell-biological transport and interaction process. Further (3) by means of pharmacologically active substances such as e.g. methyl-β-cyclodextrin, which extracts cholesterol from cell membranes, the lipid composition and thus the properties of the membranes can be purposively altered. This influence persistently affects the stability of the TNTs. Thus, a reduction of the cellular cholesterol content by 20% leads to a 40% reduction of the number of TNTs (FIG. 18). The invention thus makes available a model for finely regulating TNT mediated cell communication and if applicable to correct pathologically determined changes. Further (4) classical biochemical influences such as the alteration of their structure, the composition or the false regulation of their formation through disease, for example through diseases of the metabolism, or through medicaments, allow important diagnostic statements, in particular in the field of cytological diseases and cytological medicaments, since here communication processes play, as expected, a large role. The invention thus makes available a model for the investigation, monitoring and discovery of new pharmaceutical substances. Along with this, the discovered TNTs show surprising morphological similarities with nanotubes of phospholipid double membranes produced in vitro (Karlsson, A. et al., *Networks of nanotubes and containers*, Nature 409, 150-152 (2001)). Also with these nanotubes produced in vitro a membrane continuum is produced between the liposomes and a transportation of lipid containers can be effected via the nanotubes. It lays to hand to exploit the discovered transport principle for in vitro produced nanotubes or liposomes and for medicament targeting.

Figure 19:
FIG. 19—a fluorescence microscopy image of an extremely long and extremely sensitive TNT-like structure between two PC12 cells. PC12 cells were stained in a LabTek chamber by means of cautious addition (local application) of DiI (Molecular Probes, Oregon) to the cell culture medium. During the staining and in the simultaneous microscopic analysis destructive forms of energy (shaking, movement of the medium, too strong light incidence) were avoided as far as possible. One observed the fine membrane thread, ca. 300 μm long, with an apparent diameter of ca. 200 nm which is spanned between the cells, without touching the substrate (bar: 20 μm)

The discovered TNTs are elastic thread-like channels, surrounded by a membrane, freely stretched between the cells via the shortest path, which channels as a rule have no contact to the substrate, for example of the cell culture plate (FIG. 1). Their diameter lies in the order of less than 200 nanometers, but can however in some cases reach up to 400 nanometers. Since TNTs do not lie on the substrate and as a rule due to their length cross several focussing planes of the microscope, they are not directly recognisable as intercellular tubes in conventional microscopy processes, but are seen only as non-specific extensions or cell tubes without origin and target. The length of the new intercellular connections (TNTs) is mostly up to 50 micrometers (FIG. 1) and occasionally also up to more than one millimeter (FIG. 19). In individual cases, also branched TNTs can be observed (see FIG. 1*c*, arrow).

Figure 11:
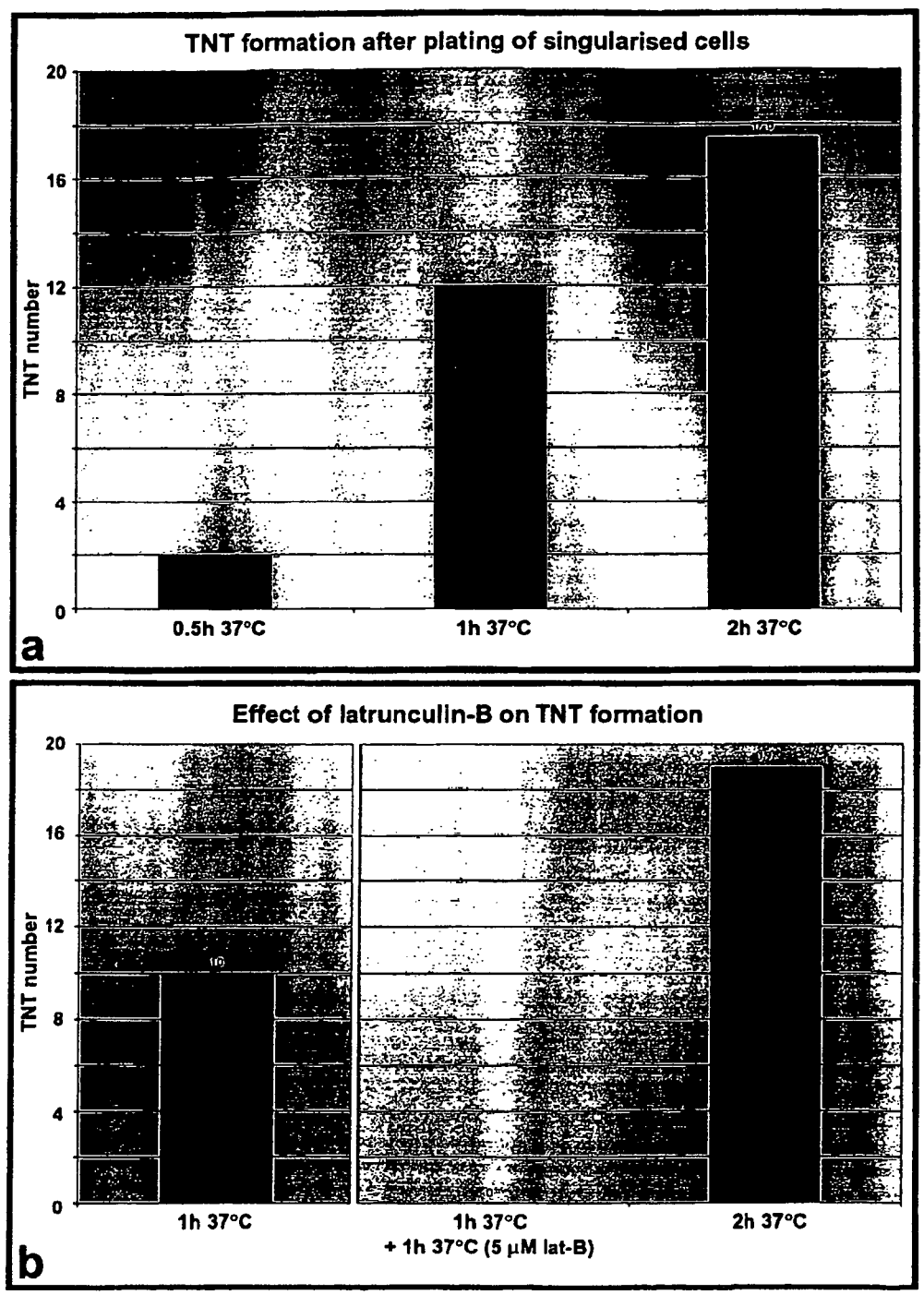

TNTs contain F-actin, but no microtubules (FIG. 1*e*, FIGS. 6*d*1-*d*3). Probably, due its high proportion in TNTs the f-actin is also involved structurally and functionally in the formation of this cell connection (c.f. FIGS. 2*a-d*). This supposition is supported by the observation that in the presence of latrunculin B, which depolymerises F-actin, TNTs no longer form and TNTs present are destroyed (FIG. 11*b*). Even if occasionally point signals of tubulin can be observed in TNTs, these do not possess the filament structure characteristic for microtubules (FIG. 1*e*). Further, in TNTs, synaptophysin, a membrane marker for "small synaptic-like microvesicles" (SLMVs, Hannah M. J. et al., *Synaptic vesicle biogenesis*, Annu. Rev. Cell Dev. Biol., 15, 733-798 (1999)) has been immunocytochemically detected at points (FIG. 3*c*,). SLMVs contain signal molecules such as acetylcholin (Bauernfeind R. et al., *Selective storage of acetylcholin, but not catecholamines, in neuroendocrine synaptic-like microvesicles of early endosomal origin*, Neuron 11, 105-121 (1993)), so that TNTs are involved in the passage of a signals between cells. Further, myosin Va (FIGS. 3d, e), an actin-dependent motor protein and Rab3a (FIGS. 3e2), a monomeric GTP binding protein, was found in TNTs. There could also be determined a partial co-localisation of myosin Va and synaptophysin-positive organelles in TNTs (FIG. 3e, open arrow). The visible organelle transport and the simultaneous presence of F-actin, myosin Va and GTP binding proteins indicates an actin or myosin mediated organelle transport (Mermall V. et al., *Unconventional myosins in cell movement, membrane traffic, and signal transduction*,Science 279, 527-533 (1998)). Further it was found that secretory granula, hormone storing organelles, are more frequently present in vitro and in vivo at the base of TNTs, FIG. 20, arrow. This allows the deduction of a functional relationship between TNTs and the endocrine system.

Figure 10:
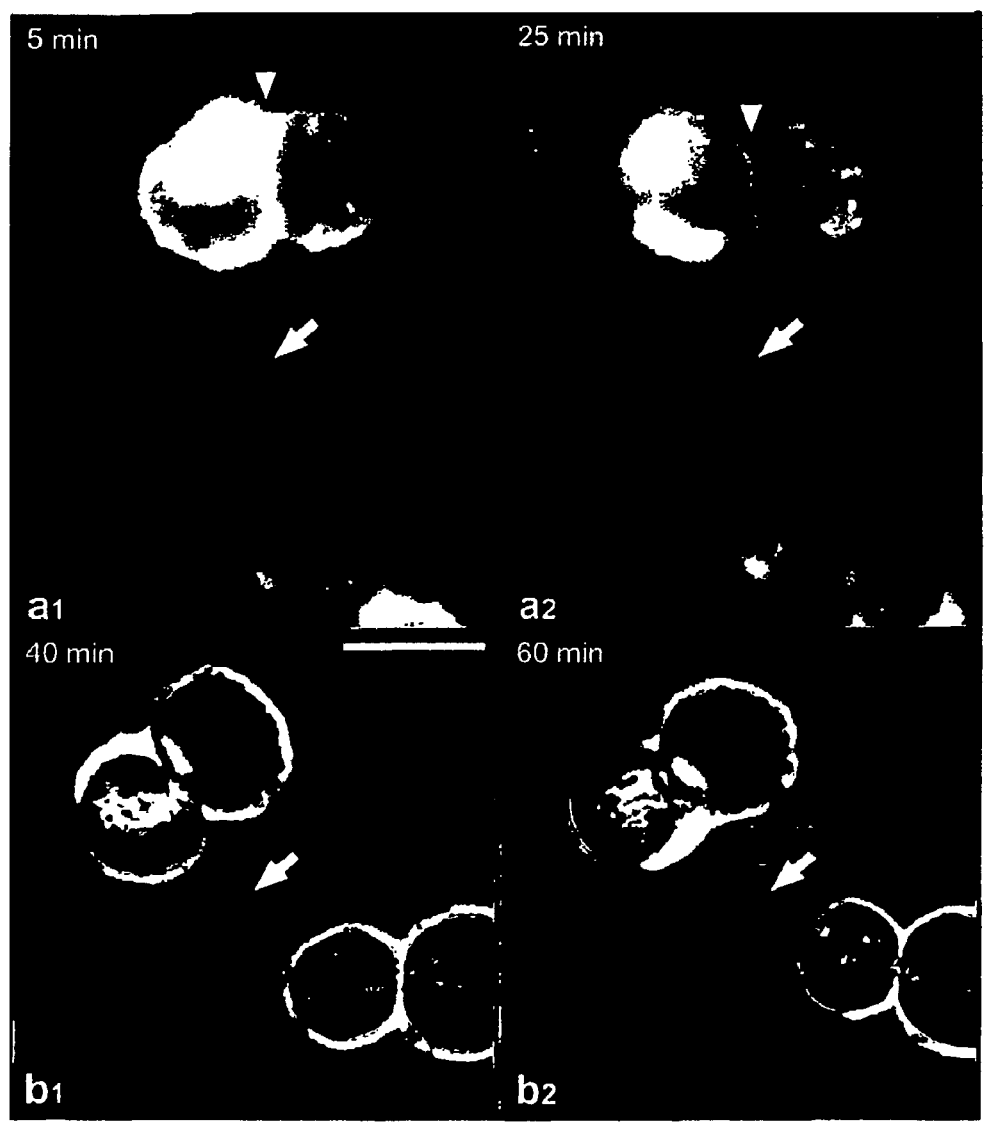
FIG. 10—time shifted fluorescence and bright field videomicroscopy images of TNTs between PC12 cells which were subject to a treatment in cell medium with 1.25% (a1, a2) or 2.5% (b1, b2) Trypsin/EDTA: the continuing trypsin/EDTA treatment leads to a detachment of the cells from the substrate (visible through the increasing rounding of the cells (arrow tips)) and finally to their detachment; over the observed period of time the TNTs remain intact (arrows). The time points of the images are indicated in minutes (min), (bar: 20 micrometers)

TNTs are very sensitive structures. Slight mechanical stress, chemical fixing or wave-like energy forms such as e.g. a few seconds of light irradiation with a wavelength of 565 nanometres allows them in many cases to tear (FIG. 9). In contrast, and differently from filopodia or axons, TNTs are not sensitive with regards to trypsin treatment (FIG. 10). TNTs rapidly form de novo between cells and could be observed only 30 minutes after the plating of PC12 cells (FIGS. 2e, f, FIG. 11a). Their number then increased strongly within the following 1.5 hours (8-fold) (FIG. 11a). Since a blocking of the cell division (G1/S phase block) in this period did not influence their formation (FIG. 12), TNTs are not a product of an incompletely developed cytokinesis.

Figure 7:
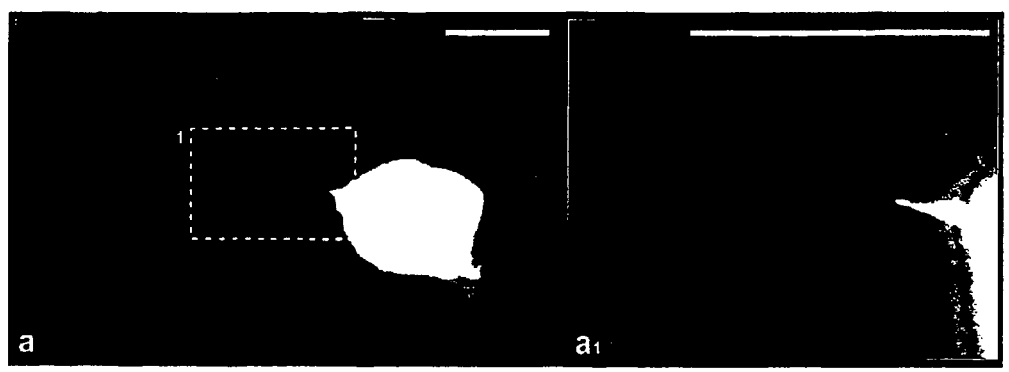
FIG. 7—cytoplasmic EYFP is not transferred between TNT-connected cells. Image in accordance with the overlay of image 3*f-i*2, but the cells of population 1 were transfected with EYFP (Clontech) and the microscopic image data not deconvolved. The signal from phalloidin stained filamentary actin is represented green, the EYFP signal red, and the CELLTRACKER™ signal blue. For the box in (a) there is shown an enlargement (a1). One notes that EYFP cannot be detected in the TNT-connected cells of population 2 (blue cells) and only half penetrates the spanning TNTs, i.e. is not efficiently transferred by means of TNTs, (bar: 10 micrometer)
Figure 14:
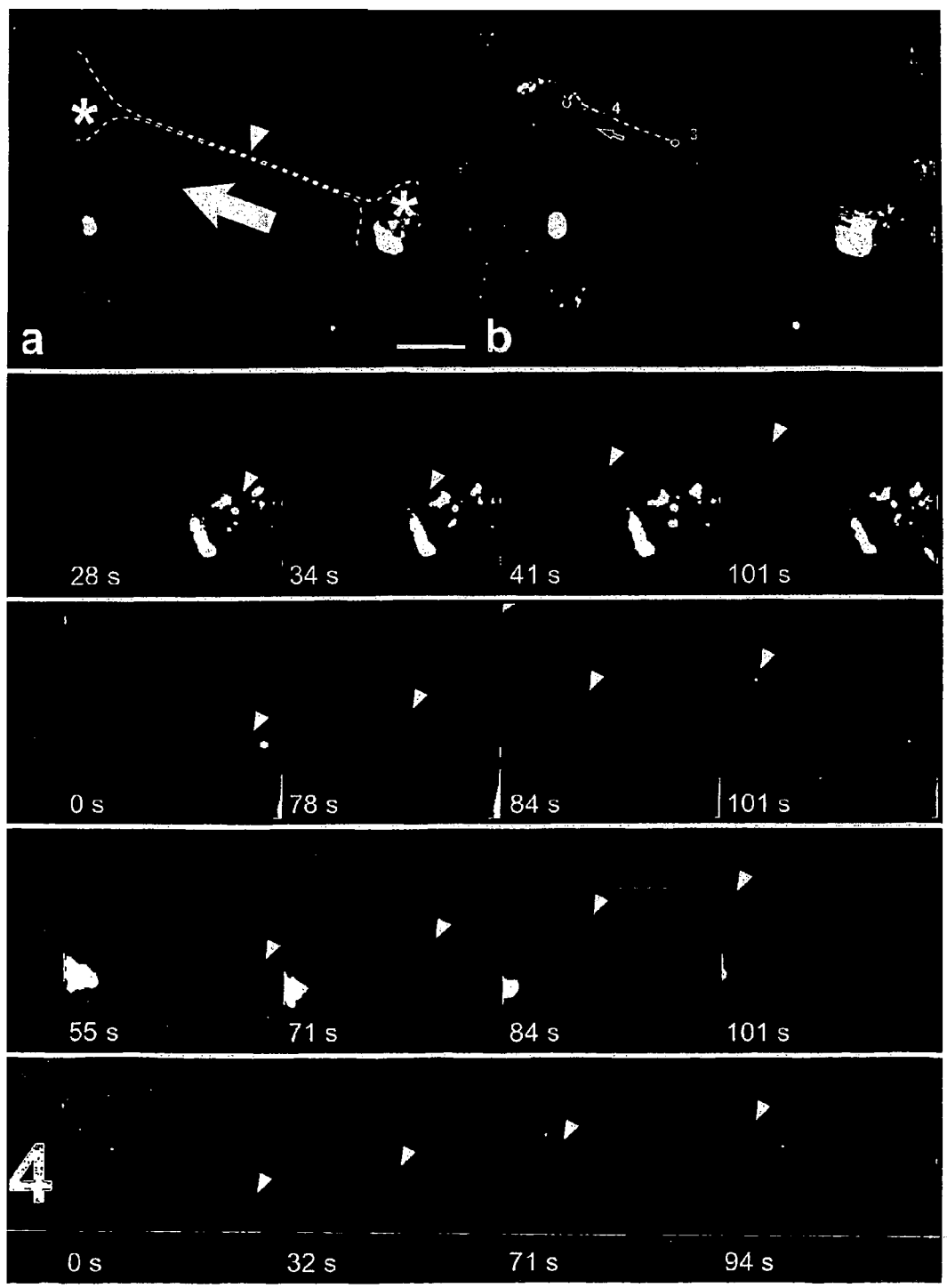
FIG. 14—direct transfer of DiI positive organelles between TNT connected cells. Image in accordance with image 4d-e. In the overview image (a) there are shown two cells (stars) connected via a TNT (arrow tips), which shows the unidirectional transfer (in the arrow direction) of DiI positive organelles. The broken lines mark parts of the cell outline. In (b) there are illustrated the partially overlapping trajectories of four representative organelles as colour coded and numbered broken lines (1-4). The coloured arrows mark the respective direction of the transfer. For each trajectory shown in (b) there are illustrated four selective individual images of the basic video sequence (series 1-4), which show the transport of the corresponding organelles (arrow tips). The time points of the images are indicated in seconds (s), (bar: 20 micrometers)

In contrast to conventional communicative cell connections such as plasmodesmata or "Gap Junctions", TNTs show scarcely measurable passive transmissibility for small microinjected dye molecules such as e.g. Calcein (FIG. 13) or BODIPY™. Likewise no significant transfer of cytoplasmically expressed EYFP or ECFP was observed (FIG. 7.) In contrast, actin, a structural component of the TNTs, was selectively transferred in the form of a GFP fusion protein (EGFP actin) between TNT connected cells (FIGS. 3j-m2). Likewise there was detected a TNT mediated intercellular exchange of farnesylated EGFP, a specific marker for the plasma membrane (FIG. 8) (FIGS. 3n-q2). As a unique feature of TNTs there was found a uni-directional transfer of membrane vesicles through these structures. These vesicles were positive for synaptophysin EGFP (FIGS. 3c, f-i2), for LYSOTRACKER™ (FIGS. 3a, b) or for the endocyted dyes DiI or DiO (Honig et al., DiI and DiO: *versatile fluorescent dyes for neuronal labelling and pathway tracing*. Trends Neurosci., 12, 331-340; Kuffler D. P., *Long-term survival and sprouting in culture by motoneurons isolated from the spinal cord of adult frogs*. J. Comp. Neurol., 302, 729-738 (1990)) (FIGS. 4d-h). The TNT mediated unidirectional transfer of DiI or DiO marked organelles from one cell to the other could be directly observed via fluorescence videomicroscopy (FIGS. 4d,e, FIG. 14). Additionally, just two hours after preparation of a mixed culture of DiI and DiO coloured cells it could be observed that different cells exchange the green and red fluorescing organelles between one another uni-directionally via TNTs (FIG. 4g1). This exchange was demonstrably not brought about via mechanisms which include the conventional endocytosis and exocytosis mechanisms. This assumption was supported by transfer experiments at 0° C., a temperature which blocks the efficient known endocytosis and exocytosis mechanisms. Under these conditions there took place reduced, in comparison to 37° C., organelle transfer, but still a significant transfer (FIG.

15). This finding supports the model of the membrane continuity between the cells (FIG. 5) formed via TNT connections.

Figure 21:
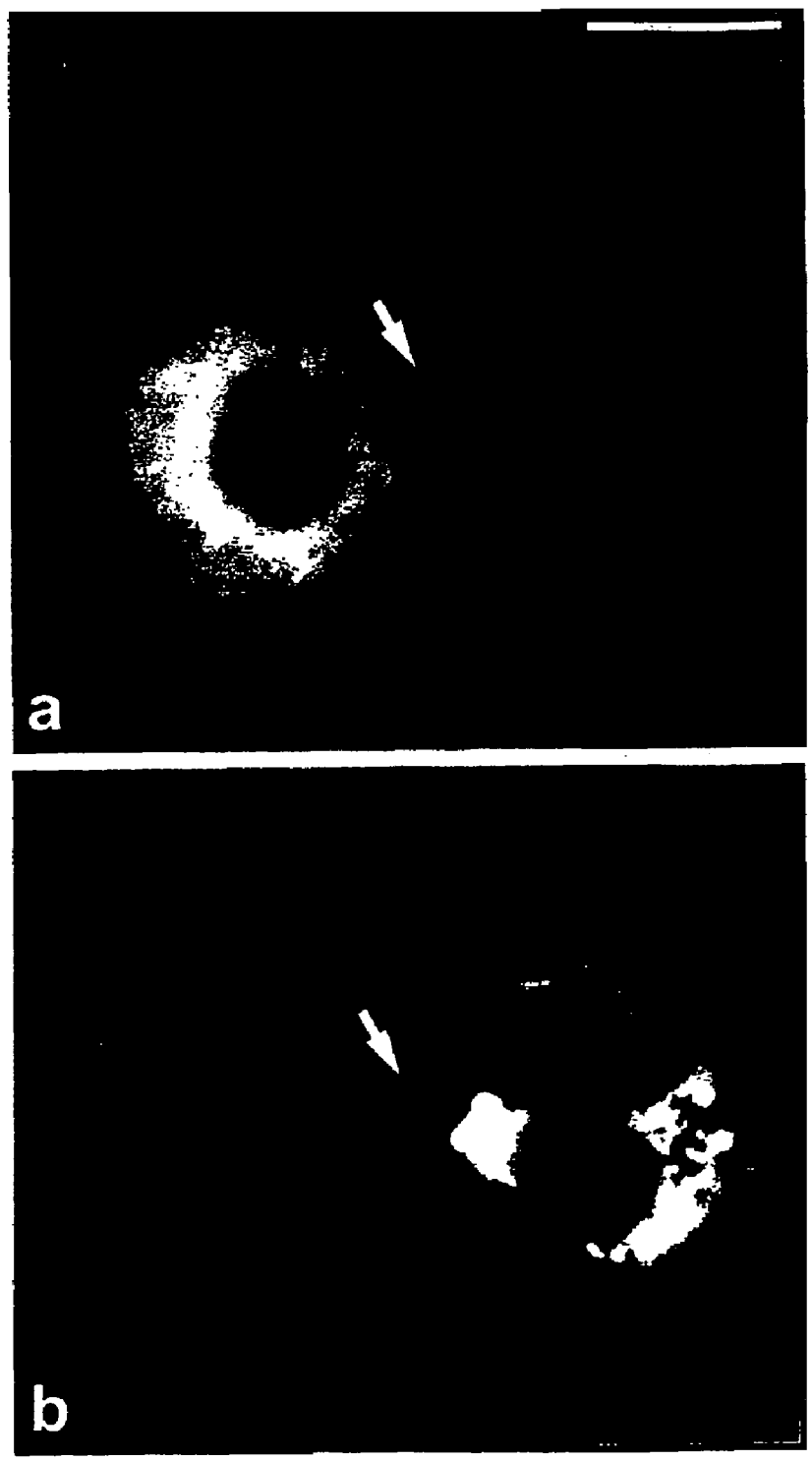
FIG. 21—Neither secretory granula nor mitochondria are exchanged between TNT connected cells. In accordance with image 3f-i2, but the cells of population 1 are transfected with chromogranin-B-EGFP (a) or EYFP-mito (b, pEYFP-mito, Clontech 6115-1). One notes that in the cells of population 2 connected via TNTs (arrows) no signals of the marker proteins employed were found.

In TNTs there could be further detected (FIGS. 2g, h), via bright field videomicroscopy, transport processes which are similar to a vesicular transport. Bright field or fluorescence microscopy showed a uni-directional transport of these structures from cell to cell with speeds from 8 to 100 nanometres per second (FIG. 2gh, FIGS. 3ab). These results together with the detection of synaptophysin positive structures (FIG. 3c) or LYSOTRACKER™ positive structures (FIGS. 3a, b) make it clear that the structures transported from cell to cell are at least partially SLMVs and/or membrane structures which belong to the endosomal system or arise therefrom. The co-localisation of the structures with myosin Va (FIG. 3e) shows that probably myosin Va is involved partially in the transport of these structures and Rab3a is involved in the regulation of the transport. Secretory granula and mitochondria were, in contrast, not observed in TNTs, or were not significantly exchanged between the cells (FIG. 21). These organelles are thus probably excluded from TNT mediated transport through size selection or other to date unknown mechanisms.

TNTs were found not only for the PC12 cell line from the suprarenal medulla of rats, but could also be detected in a kidney epithelia cell line of the vervet monkey (vero cell line) and human HEK cells (FIG. 16a) and in primary cultures of the rat obtained from medulla (FIG. 16b) and hippocampus (FIG. 16c). Thus, TNTs appear in cells which originate from highly different tissue types. Beyond this the results demonstrate that TNTs occurred not only in healthy tissue but also in cancerous tissue. It thus lies to hand that tissue type specific TNTs with specific characteristics exist. It is to be expected that TNTs are formed in particular also during the embryonal development of the cells and have an important role in e.g. pattern building. It thus lays to hand that TNTs, first, are responsible for certain forms of cell-cell communication, for example for tissue formation and maintenance, second, stand in causal connection with various diseases such e.g. cancer or viral infections, in that viral proteins such e.g. VP22 or the VSV G-protein spread via TNTs in the tissue (FIGS. 17a-d); third, due to their high sensitivity with regard to external energy forms are readily influenced and/or destructible (e.g. by light (FIG. 9)) and in this manner exert influence on complex body functions; fourth, represent purposive therapeutic starting points for many diseases which e.g. are based on the cellular network spanned through TNTs and/or their sensitivity. In this connection it was demonstrated that the removal of cholesterol from cell membranes destroys TNTs or hinders their new formation (FIG. 18) and moreover a precise regulation of their formation via a setting of the cholesterol content of membranes is possible (FIG. 18). As diseases, we mention here for example cancer and high blood pressure. There are thus provided directly the following means and therapeutica applications for the treatment of diseases.

EXAMPLES

Example 1

Means for the Therapy of Tumours

1. Influencing of TNTs by Means of External Wave-like Energy Forms

In cancer cells such as e.g. the PC12 cell line from pheochromocytoma tissue TNTs were detected after staining with WGA by means of high resolution, three-dimensional videomicroscopy imaging circa 24 hours after cell passage in accordance with Example 15 (FIGS. 1a-d). On these cells there was tested the influence of external energy forms such as e.g. visible light of a microscope system (in accordance with Example 15 Point 2) having a wavelength of 565 nanometres. Over an observation period of ca. 70 seconds it was shown that the TNT connection (FIG. 9a) is initially set into oscillation by the incident light of wavelength 565 nm (FIG. 9b), tears (9c), and within seconds winds up at the loose end like a torn elastic band (FIG. 9d). A similar effect on TNTs is also to be expected of other wave-like energy forms. Due to the sensitivity of TNTs with respect to external energy forms it suggests itself to treat in particular pheochromocytoma tumours with infrasound or ultrasound or light or magnetic field therapy. For these treatments there may be considered commercially available generators, or generators developed specifically for this application, for e.g. pulsed magnetic fields. The TNTs between the tumour cells may thus be purposively damaged. Since also healthy tissue can form intercellular thread connections, the application of these energy forms should be effected purposively and locally, in order to attain a selective damaging of the tumour tissue. The side effects of such a treatment would probably be considerably less than a corresponding radioactive irradiation or the application of chemical therapeutic means. Further, PC12 cell cultures and possibly chromaffin primary cultures in accordance with Example 16 represent suitable model systems in order to determine the most effective and selective frequencies and intensities of the employed energy forms for these therapies.

2) Purposive "Targeting" of Cytopharmacolgical or Other Components a) Targeting Via TNT Mediated Transfer of Organelles In cancer cells such as e.g. the cell line PC12 of pheochromocytoma tissue it was detected by means of high resolution three-dimensional light transmission microscopy circa 24 hours after cell passage (in accordance with Example 15) that an intercellular network based on TNTs is formed de novo (FIGS. 2a-f). Further, with direct bright field videomicroscopy (in accordance with Example 15 Point 2) uni-directional TNT mediated intercellular organelle transfer could be observed (FIGS. 2g,h). Fluorescence videomicroscopy images (in accordance with Example 15 Point 2) of these cells after staining with LYSOTRACKER™ (in accordance with Example 15 Point 5) show that fluorescing organelles are unidirectionally transferred in TNTs (FIGS. 3a, b) and are probably of endosomal origin. Fluorescence videomicroscopy images (in accordance with Example 15 Point 2) of PC12 cells after antibody staining of synaptophysin, myosin Va and Rab 3a (in accordance with Example 15 Point 4) and TRITC-phalloidin-actin colouring (in accordance with example 15 point 4) show that synaptophysin and myosin Va signals were to be found at the same position in TNTs (FIGS. 3c-e2). These in each case point-like stainings, in connection with the direct observation of the organelle transfer (FIGS. 4b, e, FIG. 14), show that in TNTs synaptophysin-positive organelles (e.g. SLMVs) are moved by motor proteins such e.g. myosin Va and that regulatory proteins such as e.g. Rab3a are involved in this transport.

Figure 15:
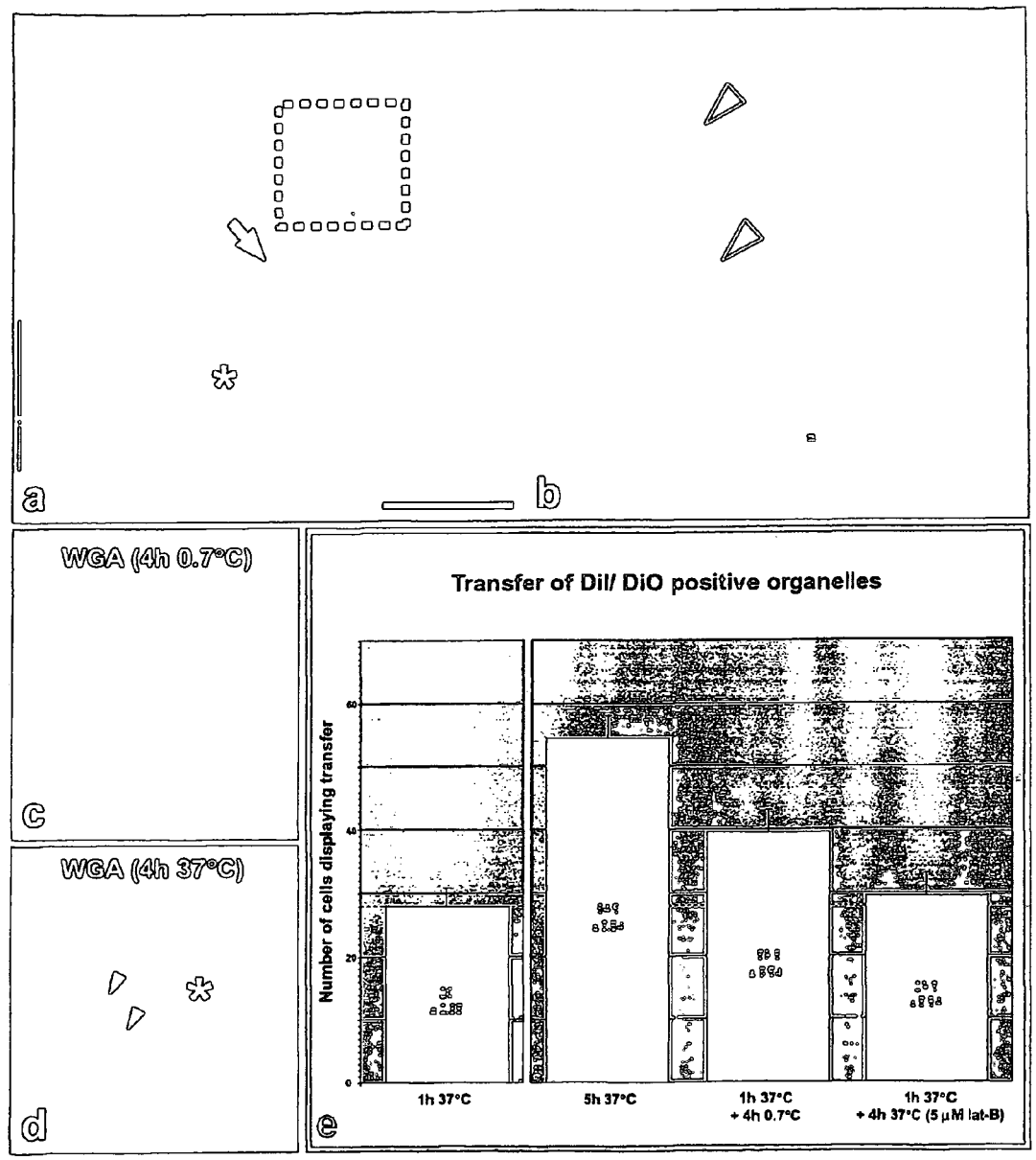
FIG. 15—a fluorescence microscopy demonstration, with the employment of a temperature block, that TNTs bring about the intercellular transfer of DiI/DiO dyed organelles in accordance with a mechanism which excludes usual endocytotic and exocytotic mechanisms. (e) two differently stained PC12 cell populations were cultivated as a mixed culture on LABTEK™ culture bowls for one hour at 37° C. and then further cultivated at various temperatures in the absence or in the presence of 5 micromolar latrunculin B (lat-B). (a) two differently staied PC12 cell populations were cultivated as a mixed culture on LABTEK™ culture bowls for one hour at 37° C. and then for four hours at 0.7° C. There can be seen one singularised double stained cell which is connected with a TNT (arrow) to the neighbouring cell (star). (B) enlargement of the boxed cell region in (a). (c, d) PC12 cells were stained with WGA one hour after plating then cultivated for a further four hours at 0.7° C. or 37° C. (d) and then analysed videomicroscopically. Cells in (c) show exclusively a plasma membrane staining, while cells in (d) additionally show a perinuclear staining (star) and also stained endocytotic structures (arrow head), (bar: 10 micrometers)

The selective exchange of endosomal or endosome-related organelles shown here between TNT connected cells represents an efficient transport system via which cytopharmaceuticals or other components can be distributed purposively and in a controlled manner in tissue assemblies such as e.g. tumours. For the purpose of demonstration, by way of example EGFP was coupled by genetic engineering to synaptophysin, which is selectively associated with endosomes and organelles related therewith (synaptiphysin-EGFP). The transfer of this fusion protein between cancer cells was documented by means of the following test procedure. A population (population 2) of PC12 cells was stained (in accordance with 15 Point 7) with CELL-TRACKER™ (Molecular Probes "blue" C-2110) and plated mixed with a further population (population 1) of PC12 cells which was transfected with synaptophysin EGFP. The mixed cell cultures were fixed 24 to 48 hours later and immunocytochemically stained with polyclonal anti-GFP antibody (Molecular Probes A-6455) and phalloidin-FITC (in accordance with Example 15 Point 4). The cells were then analysed by means of three-dimensional fluorescence microscopy and deconvolution of the taken image data in accordance with Example 15 Point 2. Synatpophysin EGFP was detected in the form of point signals selectively in TNT connected cells of population 2 (FIGS. 3f-i2), i.e. was selectively transferred between these cells. Via an analysis with DiI/DiO stained organelles in accordance with Example 14 it could be demonstrated that TNTs bring about the intercellular transfer of DiI/DiO stained organelles in accordance with a mechanism which is actin dependent, but which excludes conventional endocytotic and exocytotic mechanisms. For this purpose two differently stained PC12 cell populations were cultivated as a mixed culture on LABTEK™ culture bowls for one hour at 37° C. and then further cultivated at various temperatures in the absence or in the presence of five micromolar latrunculin-B. Cell cultures without latrunculin-B, which were stained with WGA one hour after plating and cultivated for 4 further hours at 0.7° C. or 37° C., fixed and then subject to a videomicroscopic analysis, both show a clear, TNT dependent organelle transfer (FIGS. 15a, e) although the transfer at 0.7° C., a temperature which blocks the conventional endocytotic mechanisms (FIG. 15, c.f. c and d), was less (FIG. 15e). A cellular network existing in the tumour tissue and based on TNTs thus opens up the possibility, through purposive introduction of toxic, apoptotic or immunogenic substances (substances or proteins produced by genetic engineering which in accordance with the above described example are equipped for the necessary signals for transport via TNTs), to purposively destroy or to influence in a regulatory manner the cells connected via TNTs, e.g. in accordance with Example 1 Point 1.

b) Targeting Via TNT Mediated Transfer of Membrane Components

It was shown that cancer cells form via TNTs a syncytium (FIGS. 2e, f) via which specific membrane components can be exchanged. This demonstration was carried out as follows. A population (population 2) of pheochromocytoma PC12 cells was stained (in accordance with Example 15 Point 7) with CELLTRACKER™ (Molecular Probes, "blue" C-2110) and plated mixed with a further population (population 1) of PC12 cells which was transfected with farnesylated EGFP (Clontech 6074-1). The mixed cell cultures were fixed 24-48 hours later and immunocytochemically stained with a polyclonal anti-GFP antibody (Molecular Probes A-6455) and phalloidin-FITC (in accordance with Example 15 Point 4). The cells were then analysed by means of three-dimensional fluorescence microscopy and deconvolution of the taken image data (in accordance with Example 15 Point 2). Farnesylated EGFP was selectively detected at the plasma membrane of cells of population 2 connected with TNTs (FIGS. 3n-q2), i.e. selectively exchanged between the TNT connected cells in the form of a plasma membrane transfer. As cellular network existing in the tumour tissue and based on TNTs thus opens up the possibility, through purposive introduction of toxic, apoptotic or immunogenic substances (substances or protein produced by genetic engineering which in accordance with the above described example are equipped with the necessary signals for membrane transfer via TNTs such e.g. a farnesyl anchor) purposively to destroy or regulatively to influence the cells connected via TNTs (e.g. in accordance with Example 1 Point 1).

Example 2

Means for Therapy of Diseases of the Metabolism

Also diseases of the metabolism which e.g. influence the lipid composition such as e.g. the cholesterol content of membrane have effects on the stability of the discovered TNTs (FIG. 18, in accordance with Example 16 Point 1). Their tearing causes microlesions (FIG. 9) specifically in the regions of the plasma membrane e.g. of neuroendocrinic cells, where the storage organelles for messenger substances, so-called secretory granula, are present in numbers (FIG. 20) and is thus an efficient signal for cell reactions such as the exocytosis of messenger substances such as hormones, neuropeptides or growth substances into the blood circulation or into the extracellular area. This signal may also cause an altered exocytosis rate. This can have pathological effects such as e.g. a pathologically increased hormone level, but is also therapeutically useful. Thus, the influencing of the cell communication based on TNTs in accordance with Example 16 can have signal effect, which leads to altered cell reactions and has as a consequence useful mechanisms such as e.g. apoptosis or necrosis. A defined control of the last mentioned mechanisms is also conceivable by means of a purposive setting of the TNT stability e.g. through changes of its lipid composition (in accordance with Example 16 Point 1) or their influencing via external energy forms (in accordance with Example 16 Point 2).

Example 3

High Blood Pressure

Figure 20:
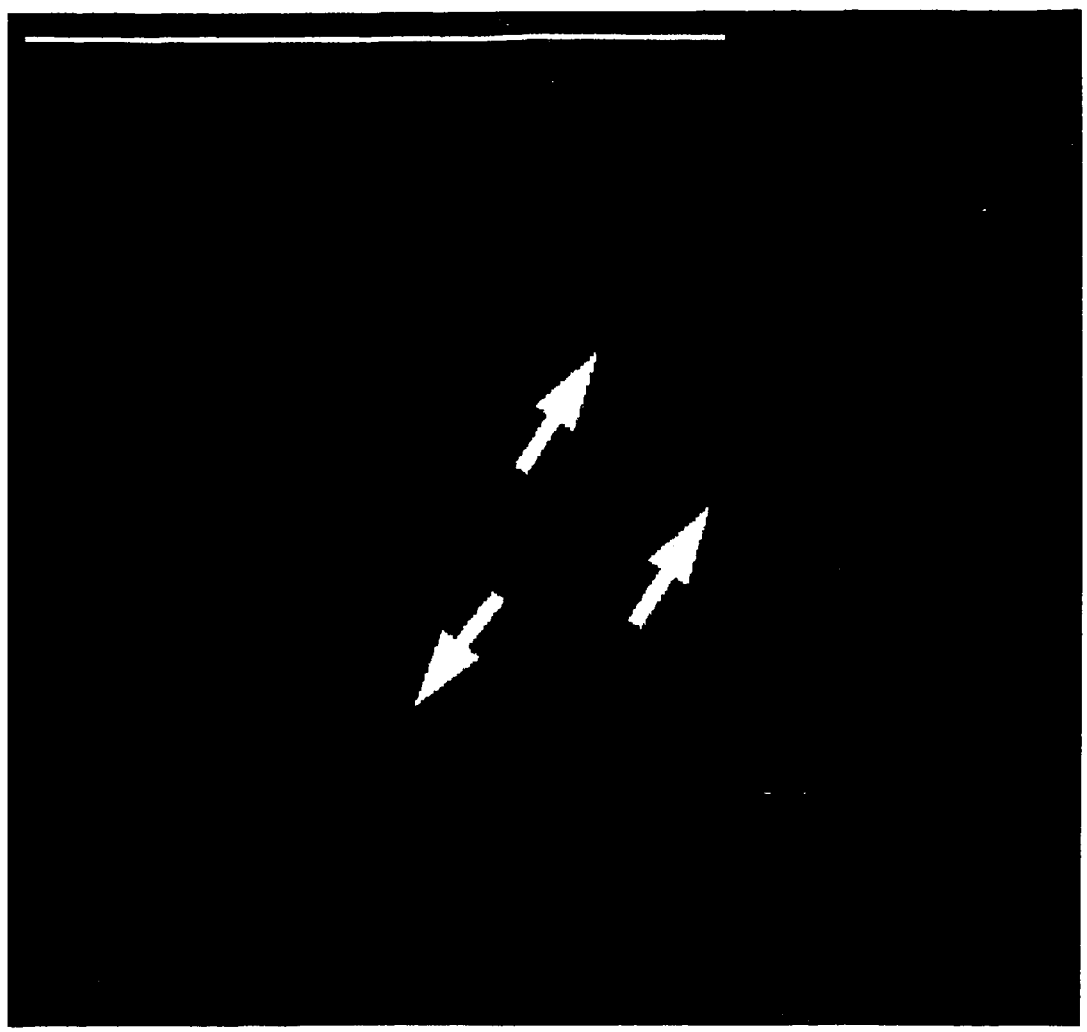
FIG. 20—a multi-colour videomicroscopy image of a WGA dyed PC12 cell 24 hours after transfection with a cDNA which coded the green fluorescing human chromogranin B-EGFP [Kaether, C, Salm, T., Glombik, M., Almers, W. & Gerdes, H.-H.: *Targeting of green fluorescent protein to neuroendocrine secretory granules: a new tool for real time studies of regulated protein secretion*, in Eur. J. Cell Biol. 1997, 74:133-142)—a marker protein characteristic for secretory granula, so that in the image the secretory granula (see arrow—light grey in the black and white image) fluoresce green and red coloured (medium grey) the plasma membranes of the cell and the newly discovered cell tubes—the incidence of secretory granula in the contact zones of the TNT connected cells strongly suggest that the TNTs are involved in the regulated hormone and neuropeptide secretion (bar: 20 micrometer)

The blood pressure is controlled inter alia by means of the hormone system such as e.g. via signal substances of the adrenal gland. A multi-colour videomicroscopy recording of a WGA stained PC12 cell of the adrenal gland 24 hours after transfection (in accordance with Example 15) with a cDNA which codes for the green fluorescencing human chromogranin B-EGFP [Kaether, C, Salm, T., Glombik, M., Almers, W. & Gerdes, H.-H.: *Targeting of green fluorescent protein to neuroendocrine secretory granules: a new tool for real time studies of regulated protein secretion*, in Eur. J. Cell Biol. 1997, 74:133-142), a marker protein characteristic for secretory granula, shows the accumulation of the secretory granula at the contact zones of the TNT connected cells (FIG. 20, arrow). This makes evident that TNTs are involved in the regulated hormone and neuropeptide secretion. The irritation or microlesion of adrenal gland cells (e.g. by means of oscillations or tearing of TNTs in this tissue (in accordance with Example 1 Point 1 or Example 16 point 2) or altered lipid composition (in accordance with Example 16 Point 1) can have as a consequence the exocytosis of messenger substances from adrenal gland cells into the blood circulation. Through this there can arise a pathologically increased adrenalin level, which in turn leads to an increased blood pressure. Options for therapy are provided through screening or elimination of the external energy forms by means of suitable screening materials (e.g. by means of the "Wave Shield" already available on the market as radiation protection for mobile telephones or special foils or wall paints from "Protect ES") and/or through influencing of endogenous factors such e.g. the lipid composition of cell membranes. The latter can be attained through altered nutrition or the application of specific medicaments, whereby in this context the cholesterol level has particular significance associated with it (FIG. 18, in accordance with Example 16 Point 1).

Example 4

Autoimmune Diseases

In the case of autoimmune diseases such as e.g. Type 1 diabetes, the immune system recognizes the bodies own proteins. This faulty behaviour is often initiated by viral proteins (molecular mimicry) or incorrectly folded proteins. It has been shown that, via TNTs, cells form a syncytium via which membrane components can be exchanged. This demonstration was carried out as follows. A population (population 2) of adrenal gland PC12 cells was stained with CELLTRACKER™ (Molecular Probes, "blue" C-2110) and plated mixed with a further population (population 1) of PC12 cells which was transfected with farnesylated EGFP (Clontech 6074-1). The mixed cell cultures were fixed 24 to 48 hours later and stained immunocytochemically with a polyclonal antibody-GFP antibody (Molecular Probes A-6455) and phalloidin FITC (in accordance with Example 15). The cells were analysed by means of three-dimensional fluorescence microscopy and subsequent deconvolution of the taken image data (in accordance with Example 15 Point 2). Farnesylated EGFP, a specific marker for the plasma membrane (FIG. 8) was selectively detected in the plasma membrane of cells of population 2 connected with TNTs (FIGS. 3*n-q*2), i.e. selectively exchanged between the TNT connected cells in the form of a plasma membrane transfer. This result demonstrates that cell surface proteins can be distributed via a cellular network existing in the tissue and based on TNTs.

In this context it could also be shown that TNTs are involved in the distribution of antigen presenting surface proteins, components of the "major histocompatibility" (MHC) complexes in tissues. For this purpose a population (population 2) of pheochromocytoma PC12 cells was stained (in accordance with Example 15 Point 7) with CELLTRACKER™ (Molecular Probes "blue" C-2110) and plated mixed with a further population of PC12 cells (population 1) which were transfected with HLA-A2-EGFP (H. J. Geuze, Department of Cell Biology, Institute of Biomembranes, UMC, Utrecht, Holland). The mixed cell cultures were fixed 24 to 48 hours later and immunocytochemically stained with a polyclonal anti-GFP antibody (Molecular Probes A-6455) (in accordance with Example 15 Point 4). The cells were then analysed by means of three-dimensional fluorescence microscopy (in accordance with Example 15 Point 2). HLA-A2-EGFP was detected in cells of population 2 connected with TNTs in the form of point signals (FIGS. 17*e, f*). In particular the fact that the MHC complexes can be carried by membranic transporters, in part related with the endosomal system, makes clear the potentional involvement of TNTs in the distribution of these complexes within the tissue. For this reason the destruction of the entire affected tissue can be prevented in that through the above mentioned external energy forms (in accordance with Example 16 Point 2) or through alteration of the lipid composition (in accordance with Example 16 Point 1) the network based on TNTs can be locally destroyed or regulatively influenced. The TNT mediated transfer of immunoreactive components in tissue structures opens up the possibility of purposively distributing such components in tissues, i.e. in this way to stimulate immune responses which as a final consequence could lead to elimination by the body on immune system.

Example 5

Prion Disease

Prion disease is initiated by a wrongly folded protein (prion protein) which is associated with the cell surface via a glycosalphosphatidylinositol (GPI) anchor and through this acts in an infectious manner in that it induces a faulty folding of the corresponding intact cellular protein. How prions pass from cell to cell is largely not understood. It has been shown that adrenal gland cells or hippocampal neurones (FIG. 16c) form, via TNTs, syncytium via which lipid anchored membrane components are exchanged in a accordance with Example 1 Point 2b (FIGS. 4a-c, FIGS. 3n-q2). The infectious prion protein associated with the plasma membrane via a comparable lipid anchor can thus be transferred to neighbouring cells via TNTs. Therapy options are thus given by destruction of the network based on TNTs by means of external energy sources in accordance with Example 16 Point 2 (FIG. 9) or though alteration of the membrane composition in accordance with Example 16 Point 1 (FIG. 18).

Example 6

General Hormone and Metabolic Disruptions

Via a three-dimensional videomicroscopic analysis of suprarenal medulla cells in accordance with Example 1 Point 2a, b there was detected an organized TNT based network between the cells via which a sycytium is formed (FIGS. 2e, f, FIGS. 3n-q2, FIGS. 4a-c) and organelles (FIGS. 4d-h, FIG. 14) transferred. Further cytoplasmic components are exchanged between cells via TNTS. This was demonstrated in that a population (population 2) of neuroendocrinic PC12 cells (in accordance with Example 15 Point 7) was stained with CELLTRACKER™ (Molecular Probes, "blue" C-2110) and mixed and plated with a further population with PC12 cells (population 1) which was transfected with EGFP actin (Fischer, M., Kaech, S., Knutti, D. & Matus, A. *Rapid Actin-Based Plasticity in Dendritic Spines*. Neuron (1998) 20: 847-854). The mixed cell cultures were fixed 24 to 48 hours later and dyed immunocytochemically with a polyclonal anti-GFP antibody (Molecular Probes A-6455) and phalloidin FITC (in accordance with Example 15). The cells were analysed by means of three-dimensional fluorescence microscopy and subsequent deconvolution of the taken image data (in accordance with Example 15 Point 2). EGF actin was selectively detected in cells of population 2 connected via TNT (FIGS. 3g-m2), i.e. was selectively transferred between the TNT connected cells. Thus, TNTs could make possible an electrical or chemical cell coupling and thereby bring about the synchronized exocytosis of messenger substances. To date, no electrical or other connection between PC12 cells could be found which is consistent with the absence of connexins, special contact proteins, in these cells. Although the exciting splachnic nerve only partially forms synaptic contacts with the suprarenal medulla cells there occurs a synchronous cell response of the suprarenal medulla. This principle of cell coupling via TNTs may also be valid for other body or glandular tissues. The missing synchronization of the adrenal gland cells after the tearing of the TNTs e.g. by light (FIG. 9) could have as a consequence a secretion of signal substances which is not adapted to the physiological requirements and could thus be causal for many hormonal and metabolic diseases. These metabolic disruptions could be treated in accordance with the methods indicated in Example 3 such as e.g. the screening from external energy forms and/or the influencing of endogenic factors such as e.g. the alteration of the cell membrane composition (in accordance with Example 16 Point 1) via the application of specific pharmaceuticals. A therapy by purposive stimulation of the TNT formation, e.g. via the expression of viral protein such as e.g. VSV G-ECFP (FIG. 17d) is conceivable.

Example 7

Means for Improving or Providing New Gene Therapeutic Methods

A central point for gene therapy is the purposive distribution of reactive components in tissue structures. This is pursued e.g. with the coupling of such components to the viral VP22 protein, which is efficiently transferred from cell to cell in accordance with a previously unknown mechanism. For this purpose, the transfer mechanism is investigated with regard to involvement of TNTs. 24 hours after transfection of PC12 cells with VP22-GFP the cells were analysed by means of video fluorescence microscopy (in accordance with Example 15). There were found strongly fluorescent TNT connections between the cells (FIGS. 17a-c). Within these connections fluorescing vesicular structures were visible which change their position in the course of the observation. This finding documents a TNT dependent transfer of the viral protein between the cells. Due to their property of making possible the transport of specific therapeutically significant molecules such as e.g. VP22, TNTs and the influencing thereof represent important options for improving gene therapeutic methods or even to create new methods. For example through stimulation of TNT formation through e.g. expression of viral proteins such as of the VSVG protein (FIG. 17d), in accordance with Example 8) or the influencing of TNTs (in accordance with Example 16) influence can be had on the intercellular transport of therapeutic agents. The possibility of locally applying the energies necessary therefor (e.g. sound, electromagnetic fields, light) or pharmaceuticals, offers the prospect of a local control of the therapeutic agents. Through the purposive introduction of therapeutic substances, which are equipped with the necessary signals for transport via TNTs a purposive and efficient distribution in the tissue in accordance with Example 1 Point 2 can be attained.

Example 8

Means for the Therapy of Infections with Pathogens

Along with the transfer of viral VP22 in accordance with Example 7, by means of a fluorescent microscopy analysis of neuroendocrinic PC12 cells 48 hours after transfection (in accordance with Example 15) there was detected (FIG. 17d) the intercellular transfer of a further viral fusion protein, VSVG-ECFP (Rustom, A., Bajohrs, M., Kaether, C., Keller, P., Toomre, D., Corbeil, D., Gerdes, H.-H.: *Selective delivery of secretory cargo in Golgi-derived carriers of non-epithelial cells*, in Traffic 2002, 3: 279-288). Beyond this, there was observed in VSVG expressing cells a stimulating effect on the TNT formation. It is to be presumed that also other pathogenic proteins or pathogens than the model viruses investigated here spread in tissue via TNTs. Thus, TNTs represent ideal points of attack for therapies which prevent the distribution of pathogens in tissue. Purposive destruction of the TNTs by means of local application of the energy forms necessary therefor or pharmaceuticals in accordance with Example 1 and Example 16 can thus reduce or even prevent the distribution of pathogens. By means of influencing the membrane composition as e.g. by means of pharmaceuticals in accordance with Example 16 Point 1, which alter e.g. the cholesterol content of the membrane and therewith the stability of the TNTs (FIG. 18), or by means of purposive changes in nutrition, preventive measures for hindering viral and bacterial infection can be found.

Example 9

Subtle Physiological and Psychologically Effects

The ultrasensitive TNTs may, due to their extreme sensitivity, be responsible for the perception of the external energy forms such as e.g. infrasound, ultrasound, light or magnetic fields or also internal irritations. This assumption was supported by the observation that e.g. through the relatively energy-poor excitation with light of the wavelength 565 nm during the microscopic analysis, TNTs were excited to microscopically resolvable oscillations and in many cases tear (FIG. 9). Such vibrations or the tearing of TNTs could induce diverse cellular reactions. In the case of irritation of suprarenal gland cells this can lead to an increase of the neuroendocrine secretion and as a consequence e.g. to high blood pressure. This is supported by the observation that secretory granula, which store neuropeptides and hormones are locally concentrated (FIG. 20) in the contact zones of the cells connected by TNTs. The substances released into the blood circulation e.g. from the adrenal gland contain components which both act on the physiological processes of other organs and tissue types and also alter the synaptic plasticity of neural networks in the central nervous system. It is conceivable that this has the consequence of subtle physiological and psychological effects. Examples of such effects include general complaints such as feeling unwell, agitation, sleep disruptions and nervousness up to schizophrenic behaviour patterns and also unconscious reactions to water courses, radiation from mobile telephones, high tension power lines, industrial facilities and as far as parapsychological effects. Opportunities for therapies are provided through influencing of the TNT connections or their formation, in accordance with Examples 2, 3, 6 and 8 (screening or elimination of external energy forms, influencing of the lipid composition of the cell membrane, induction of formation of TNTs).

Example 10

Tissue Engineering

Figure 12:
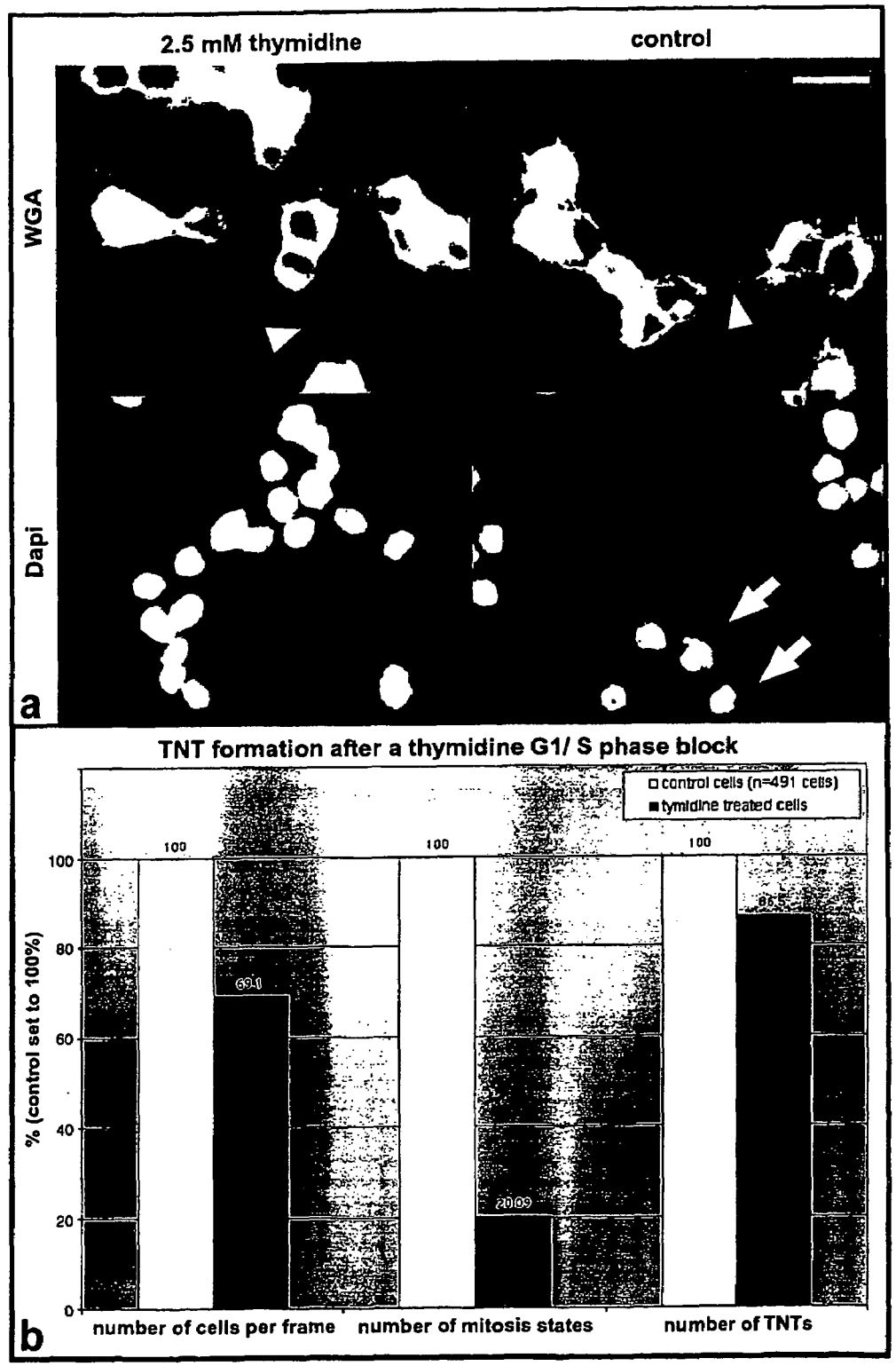

Via a three-dimensional videomicroscopic analysis of suprarenal medulla cells in accordance with Example 1 point 2a, b there was detected the formation of an organized TNT based network between the cells, via which a syncytium arises (FIGS. 2e, f, FIGS. 3n-q2, FIGS. 4a-c) and organelles can be unidirectionally transferred (FIGS. 4d-h, FIG. 14). TNTs were, in accordance with Example 16 found in all to date investigated cells structure systems such as PC12 cells, HEK cells (FIG. 16a) and primary cultures of the medulla (FIG. 16b) and of the hippocampus (FIG. 16c). With a special colouring method, moreover, very long TNTs have been found. For this purpose PC12 cells were stained in a LABTEK™ cell culture bowl by means of the cautious addition (local application) of Dil (Molecular probes, Oregon) to the cell culture medium. During the colouring and the simultaneously occurring microscopic analysis (in accordance with Example 15) disruptive energy forms (shaking, movement of the medium, too strong light incidence etc.) were as far as possible avoided. The analysis shows TNTs which link the individual cells over distances of more than 1 mm (FIG. 19). The formation of TNTs thus represents a significant component for tissue formation in developing or adult organisms. It has been shown that TNTs do not arise from the cell division via an incomplete cytokinesis, but are formed de novo (FIGS. 2a-d). For this purpose PC12 cells were analysed for the formation of TNTs after 14 hour treatment with 2.5 mM thymidin in the cell culture medium which blocks the cells in the G1/S phase of the cell cycle and prevents a division, or under control conditions, i.e. without the presence of thymidin, passaged and analysed one hour later (in accordance with the Example 15) after staining with WGA, 20 minutes fixing in 4% paraformaldehyd/4% sucrose, 3 minutes treatment with 0.2% TRITON™ X-100 and nucleus staining with Dapi (FIG. 12). These results imply that tissue engineering in vitro strongly depends upon the formation and/or the maintenance of TNTS. That applies not only for strongly proliferating cells but also for slowly growing or post-mitotic cell cultures. This in turn makes it evident that a control of in vitro tissue cultures can be attained through modulation of the TNT connections. This modulation is based on their characteristic properties on which influence can be purposively effected in accordance with Example 16 through external energy forms such as e.g. light (FIG. 9) or alteration of the lipid composition such as e.g. the withdrawal of cholesterol (FIG. 18).

Example 11

Computer Supported Neural Networks

In accordance with Example 10 there was detected the formation of an organized TNT based network between the cells, via which a syncytium arises (FIGS. 2e, f, FIGS. 3n-q2, FIGS. 4a-c) and information is unidirectionally exchanged between individual cells (FIGS. 4d-h, FIG. 14). In accordance with Example 16, TNTs were also found in neural primary cultures (FIG. 16c). Thus it is to be presumed that TNTs represent a decisive component of the information processing neural system. Computer supported neural networks are based on the simulation of such neural networks of the central nervous system. The potential of such network simulations for future technology is estimated to be very high, although the systems realized to date are still very strongly limited in their functions in comparison to the central nervous system. Via the connection pattern of TNT connected cells which has been discovered, in combination with the unidirectional transfer of information, there arises the possibility of markedly improving present computer supported networks by taking into consideration the connections based on TNTs and their characteristic properties, or to develop new systems.

Example 12

Staining Methods and Characterisation of TNTs

Figure 2:
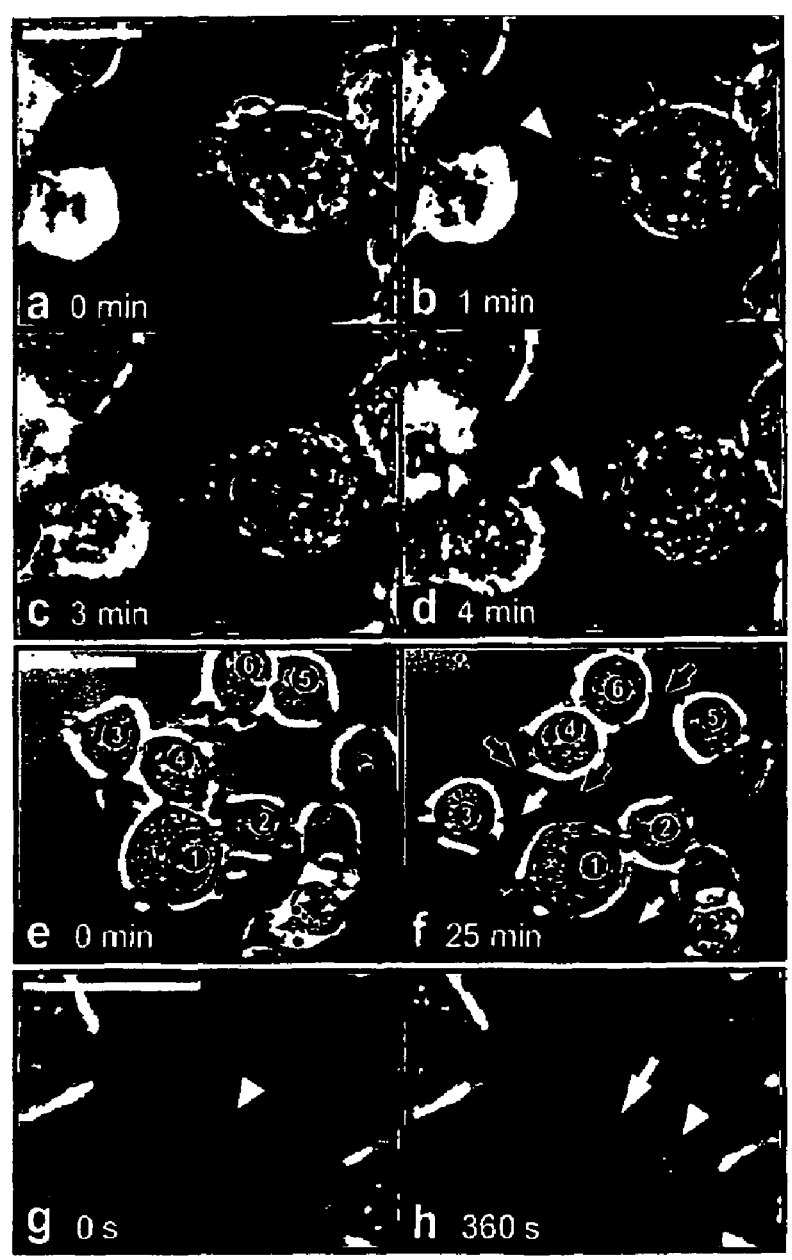
FIGS. 2a-d—time shifted bright field videomicroscopy images of de novo formed TNTs in various stages 2 hours after plating out of PC12 cells: a) dynamic projections on one cell; b) the projection marked by means of an arrow tip meets a neighbouring cell in c) and forms a TNT (arrow); indicated time in minutes (min), (bar: 20 micrometers)
FIGS. 2e, f—time-shifted bright field video microscopy images of the formation of a TNT network in PC12 cell culture: on the one hand TNTs (black arrows)—probably already existing—between cells running away from one another are visible and new TNTs (white arrows) are formed, so that a complex network arises (images are superpositions of three (x-y) individual section planes and show all detectable TNTs; the same cells are similarly numbered: time indication in minutes (min), (bar: 20 micrometer)
FIGS. 2g, h—first and last individual image of a direct bright field videomicroscopy sequence, which over a time period of 360 seconds from unidirectional, intercellular organelle transport (arrow tip) in the TNTs stretched between two PC12 cells, ca. 50 minutes after cell passage—the transport speeds were between 8 and 100 nm per second. The arrow marks the initial point of the translocation, (bar: 20 micrometer)
Figure 3:
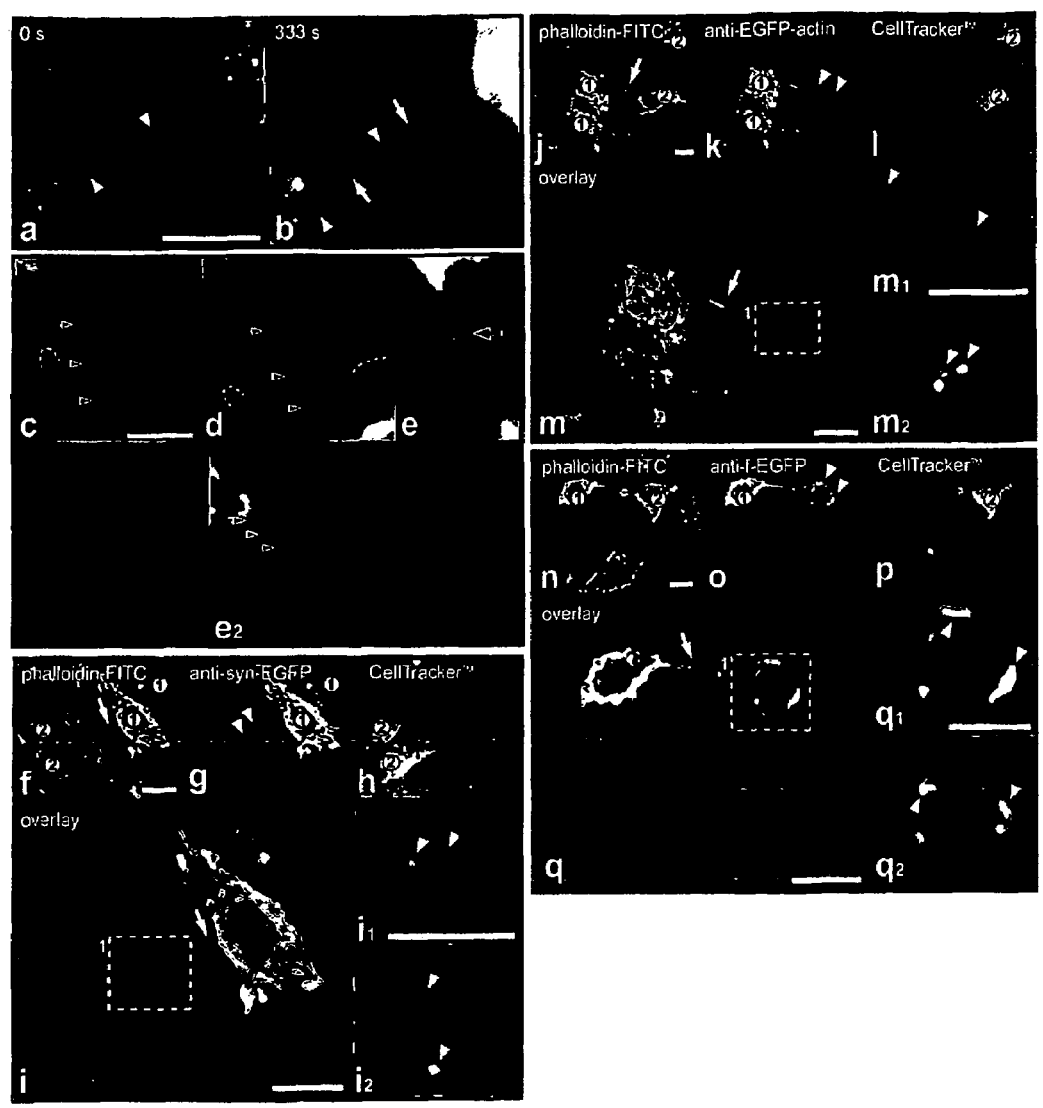
FIGS. 3a,b—fluorescence video microscopy images of PC12 cells after staining with LYSOTRACKER™—the fluorescing organelles (arrow tips) are moved unidirectionally in the TNT, whereby arrows mark the initial points of the objects, (bar: 10 micrometers)
FIGS. 3c-e2—fluorescence video microscopy images of PC12 cells after antibody staining of synaptophysin (green in c, e), myosin Va (green in d and red in e) and Rab 3a (green in e2) and TRITC phalloidin actin staining (red in c, d, e2 and blue in e)—open arrow tips mark point signals and broken lines parts of the cell edges; synaptophysin and myosin Va signals were to be found at the same positions (open arrow in e); the point-like colorations make clear that in TNTs synaptophysin positive organelles (e.g. SLMVs) are moved by motor proteins such as e.g. myosin Va and regulatory proteins such as e.g. Rab3a take part in this transport; (bar: 10 micrometers)
FIGS. 3f-i2—TNT mediated transfer of synaptophysin EGFP. A population of PC12 cells was stained with CELLTRACKER™ (Molecular Probes, "blue" C-2110) (population 2) and plated out mixed with a further population of PC12 cells (population 1) which were transfected with synaptophysin EGFP (syn-EGFP). The mixed cell cultures were fixed 24 to 48 hours later and stained immunocytochemically with a polyclonal anti-GFP antibody (Molecular Probes A-6455) and phalloidin-FITC. The cells were analysed by means of three-dimensional fluorescence microscopy and subsequent deconvolution of the image data. In the individual channel images there are represented corresponding (x-y) individual sections through cells of both populations bonded with TNTs (arrows) (upper image row, numbers mark the corresponding cell populations). One sees that synaptophysin EGFP in the form of point signals is selectively detected in TNT connected cells of population 2 (arrow tips) i.e. was selectively transferred between the cells. In the overlay of the individual channels, the phalloidin signal is green, the synaptophysin signal is red and the CELLTRACKER™ signal blue. For the boxed area there is represented an enlargement of the corresponding (i1) and also an additional (x-y) individual sectional plane (i2), (bar: 10 micrometers)
FIGS. 3*j-m*2—TNT mediated transfer of EGFP actin. Illustration in accordance with illustration 3*f-i*2 but the cells of population 1 were transfected with EGFP actin (EGFP-actin, Fischer, M., Kaech, S., Knutti, D & Matus, A. *Rapid Actin-Based Plasticity in Dendritic Spines*. Neuron (1998) 20: 847-854). One notes that EGFP actin was selectively detected in cells of population 2 (arrow tips) connected via TNT, i.e. was selectively transferred between the TNT connected cells.
FIGS. 3*n-q*2—TNT mediated transfer of farnesylated EGFP (f-EGFP). Image in accordance with image 3*f-i*2 but the cells of population 1 were transfected with f-EGFP (PEGFP-f, Clontech 6074-1). One notes that f-EGFP was selectively detected (arrow tips) at the plasma membranes of cells population 2 connected with TNTs, i.e. was selectively exchanged between the TNT connected cells in the form of a plasma membrane transfer.
Figure 4:
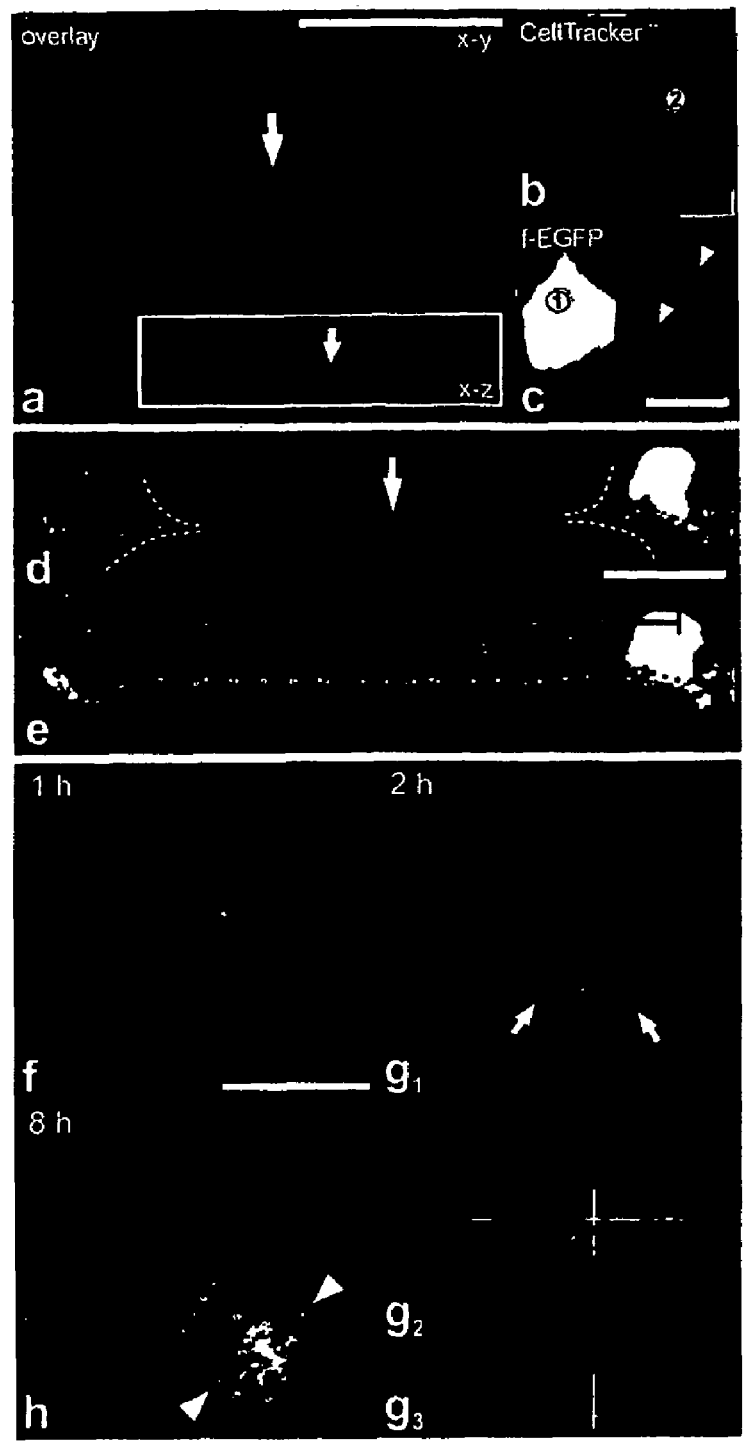
FIGS. 4*a-c*—TNT mediated transfer of farnesylated EGFP (f-EGFP) observed in living cells. A population of PC12 cells was dyed with CELLTRACKER™ (Molecular Probes, "blue") (population 2) and plated out mixed with a further population of PC12 cells (population 1) which was transfected with f-EGFP (Clontech). The mixed cell cultures were analysed 48 hours later by means of three-dimensional fluorescence videomicroscopy. In the individual channel images (b, c) there are represented corresponding (x-y) individual sections through cells of the two populations connected with TNTs (numbers mark the corresponding cell populations). In the overlay of the individual channels the f-EGFP signal is represented green and the CELL-TRACKER™ signal blue. The insert box in the superposition shows a corresponding (x-z) individual section through the marked TNT (arrow). One notes that f-EGFP is detected as plasma membrane signal in cells of population 2 (arrow tips), i.e. was selectively transferred between the TNT connected cells in the form of a plasma membrane transfer (bar: 20 micrometer)
FIGS. 4*d-e*—direct transfer of DiI positive organelles between TNT connected cells. The PC12 cells were stained with DiI and plated out on LABTEK™ culture bowls (see Example 14). The cells were then analysed by means of fluorescence videomicroscopy. There are shown individual images of three video sequences, which show the unidirectional transfer of a plurality of DiI positive organelles between two cells connected via a TNT (arrow). Of four representative organelles, their partially overlapping trajectories are illustrated (arrows 1-4). Broken lines mark parts of the cells outlines (for details see FIG. 14), (bar: 20 micrometer)
FIGS. 4*f-h*—confocal, three-dimensional fluorescence microscopy images of the transport between two mixed PC12 cell populations, each respectively stained with DiI (red) and DiO (green), at different points in time after plating of singularised cells: f) one hour old cells correspondingly contain either only DiI or only DiO positive vesicles; g1) after two hours some cells contain both DiI and also DiO positive structures (arrows); g2 is a three-dimensional analysis of the associated (x-y) or (x-z) individual section (g3) of the cell from g1 and shows that DiI positive organelles are located within one of the DiO marked cells; h) 8 hours later some cells largely contain vesicles (arrow heads) which are positive for both stains (yellow), (bar: 20 micrometers)
Figure 6:
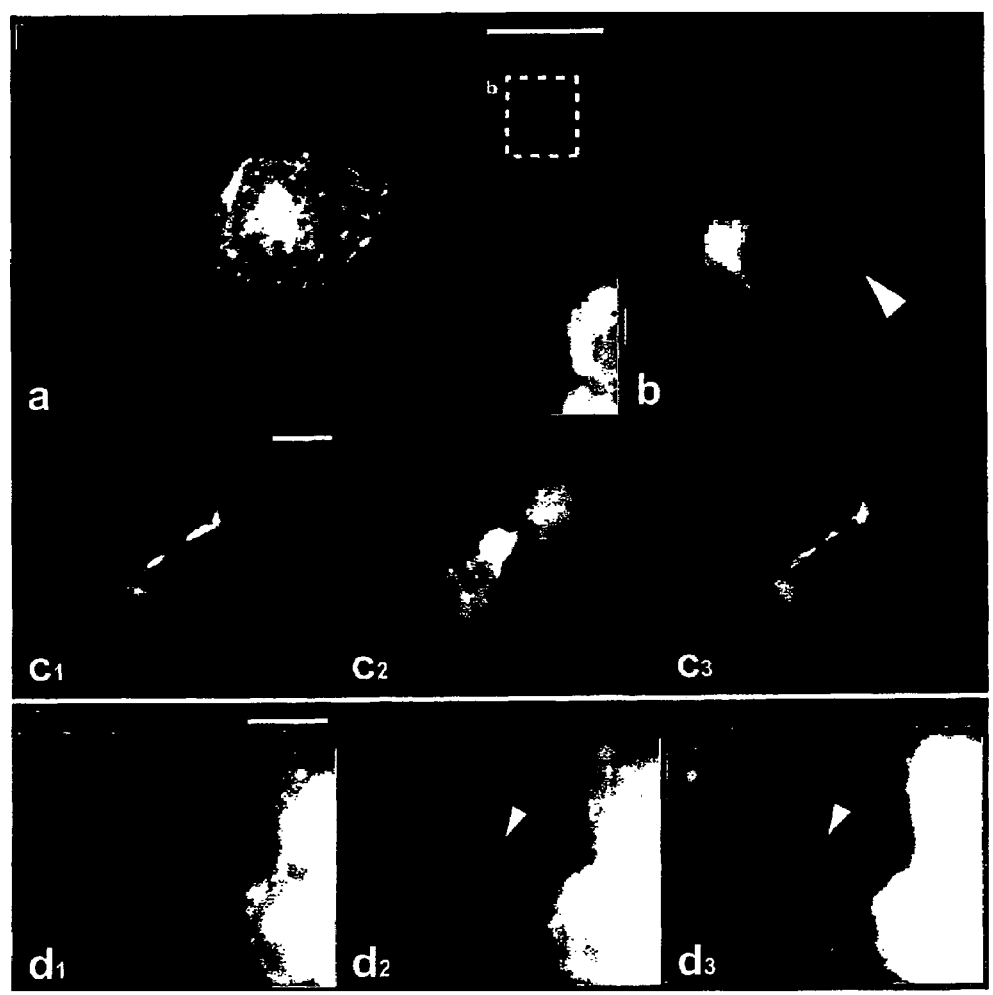
FIG. 6—TNTs contain filamentary actin but no microtubules. PC12 cells were fixed with glutaraldehyde 24 hours after plating (for details see FIG. 1*f*), stained immunocytochemically with antibodies against Alpha-tubulin (a, b, c1, d1) and with phalloidin FITC (c2, d2) and then analysed by means of fluorescence microscopy. One noted the fine microtubular strands in the filopodia of the cells (a). One such region (box in a) is shown to a larger scale in (b) and the arrow tips mark a microtubular strand. In cells which were fixed during cytokineses the bonded microtubules are to be observed in the "midbody" region (c1) and the contractile actin ring between the cells (c2). (c3) shows a superposition of the images from (c1) and (c2). With TNT connected cells (d1-d3) it emerges that in the TNT (arrow tips) no microtubules (d1) can be detected but in contrast filamentary actin (d2) can be detected (compare also FIG. 1*e*). (d3) shows a superposition of the images from (d1) and (d2), (bar: 10 micrometers).
Figure 8:
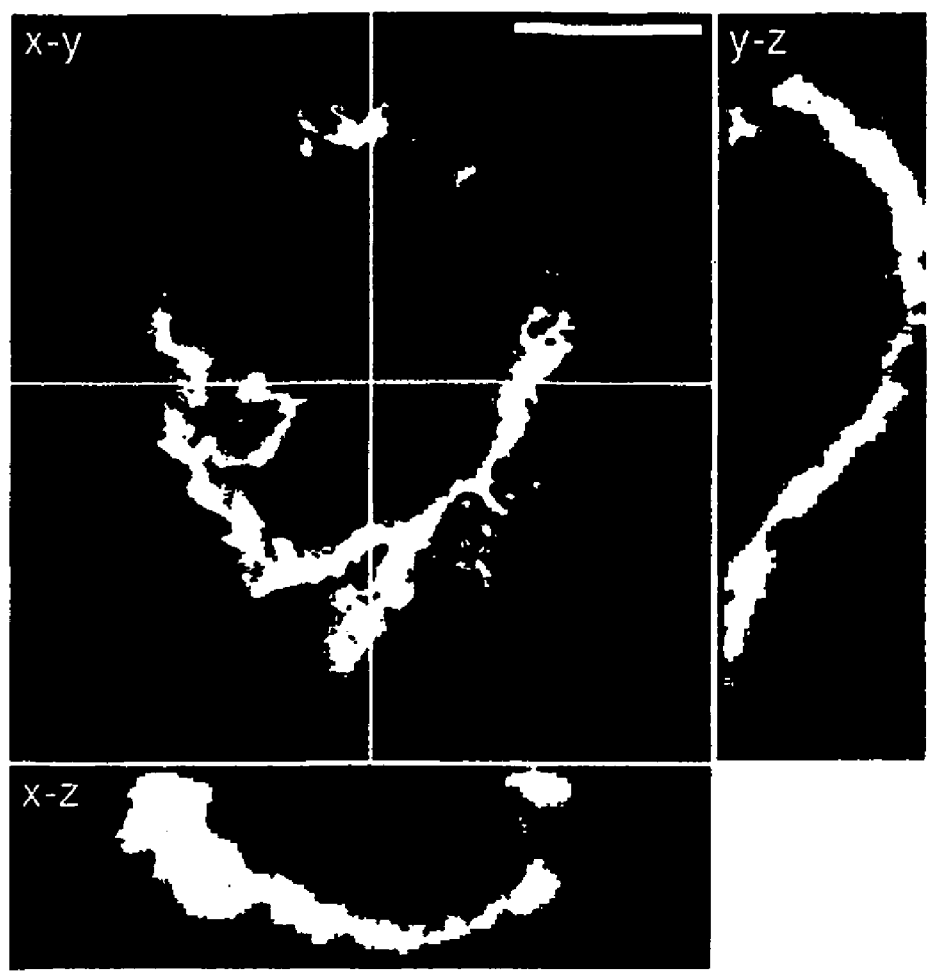
FIG. 8—farnesylated EGFP (f-EGFP) is a very specific plasma membrane marker. PC12 cells were prepared for microscopic analysis in accordance with FIGS. 3*n-q*2. f-EGFP expressing cells were then analysed by means of three dimensional confocal fluorescence microscopy. There is shown an (x-y) individual section and also corresponding (x-z) and (y-z) individual sections (the respective section planes are illustrated as lines in the (x-y) individual section) through the middle of a cell. One notes that f-EGFP is exclusively localized at the cell plasma membrane, (bar: 10 micrometers)

Our investigations demonstrated that TNTs can be made visible in vivo with WGA (FIGS. 1a-d) and also by means of transfection with plasmids which code for GFP coupled vesicular stomatitis virus G protein (viral transmembrane protein) (FIG. 17d), for EGFP actin (FIGS. 3j-m2) or for farnesylated EGFP (FIGS. 3n-q2, FIGS. 4a-c), a very specific plasma membrane marker (FIG. 8). Further, TNTs could be visualized in vitro after cautious fixing through colouring of actin with phalloidin (FIG. 1e). It was found that in contrast to axons and many filopodia, TNTs contain exclusively actin and no microtubules (FIG. 1e, FIG. 6). For this demonstration PC12 cells were fixed with glutaraldehyde (in accordance with FIG. 1f) 24 hours after plating, stained immunocytochemically with antibodies against alpha-tubulin (FIGS. 6a, b, c1, d1) and with phalloidin FITC (FIGS. 6c2, d2) and analysed by means of fluorescence microscopy (in accordance with Example 15). Microtubule strands are to be seen in the filopodia in the cells (FIGS. 6a, b) and in bonded form in the "Midbody" region (FIG. 6c1) of cells, which were fixed during the cytokinesis, and thus have the contractile actin ring between the cells (FIG. 6d2). With TNT connected cells it becomes clear that in the TNT no microtubules (FIG. 6d1) can be detected but in contrast however filamentary actin (FIG. 6d2) can be detected. With the exception of actin (FIGS. 3j-m2), TNT mediated intercellular transfer of soluble nonpolymeric cytoplasmatic substances has so far not been shown. For low molecular weight dyes such as e.g. BODIPY™ or Calcein AM, TNTs are probably not transparent (cf. FIG. 13). This observation could also explain why TNTs were not visible during microinjection studies of these or similar dyes or why no transfer of these dyes could be observed. The strongly restricted TNT mediated transfer of small molecules such as calcein and cytoplasmatic expressed proteins such as e.g. EYFP (FIG. 7) and probably also ions, is in agreement with the thus far not demonstrable electrical coupling of TNT connected cells ("patch-clamp" method). In contrast, TNT mediated transport of small organelles/vesicles, actin and plasma membrane components such as e.g. farnesylated EGFP from cell to cell was observed (FIGS. 3, 4). In contrast to filopodia and axons, TNTs are not sensitive with regard to trypsin treatment (FIG. 10). This was shown through time shifted fluorescent bright field videomicroscopy images of TNTs between PC12 cells, which were subject in cell medium to a treatment with 1.25% (FIGS. 10a1, a2) or 2.5% (FIGS. 10a1, b2) trypsin/EDTA. The continuing trypsin/EDTA treatment leads to release of the cells from the substrate, visible through the increasing rounding of the cells, and finally to their release (FIG. 10). The TNTs remain intact over the observed period of time (FIG. 10).

Example 13

Microscopic Analysis

PC12 cells (Heuman R. et al., *Relationssship between NFG-mediated volume increase and "priming effect" in fast and slow reacting clones of PC12 pheochromacytoma cells*, Exp. Cell Res. 145, 179-190 (1983) were cultivated in LabTek™ cell culture vessels at optimal density (see Rudolf R. et al., *Dynamics of immature secretory granule: role of cytoskeletal elements during transport, cortical restriction and F-actin-depending tethering*. Mol. Biol. Cell, 12, 1353-1365 (2000)). The cell culture medium contained DMEM, 10% horse serum (Gibco), 5% fetal calf serum (Gibco), 4 millimolar Glutamine. One culture vessel was treated with e.g. pharmacological substances or other influences (e.g. external energy forms). A control vessel was held under standardised conditions. After the experiment, control and test cells were stained with WGA (see following example) and analysed for TNTs. For this purpose an automatic three-dimensional videomicroscopy of living cells was carried out. For this purpose there were taken, in freely definable regions of the cell culture vessels, three-dimensional image sequences of the cells. The microscope system included for this purpose a programmable microscope table, an autofocus device, a Z-stepper and suitable control software. In contrast to two-dimensional analyses, with the aid of this three-dimensional sequence of images the number and appearance of the TNTs could be precisely determined. Through the application of GFP fusion proteins or other viral fluorescent colouring for selective marking of particular membranous structures exchanged via TNTs, a quantitative analysis of this exchange could be effected by means of the described automated three-dimensional microscopy of living cells. This method was effected with single colour or multi-colour analysis. An analysis of TNTs in cell cultures was also possible after cautious fixing and subsequent dyeing with e.g. phalloidin which in our opinion is however less dependable, since the harsh fixing methods led partially to a destruction of TNTs and altered differences present between test and control cells.

Example 14

FACS Analysis

Two PC12 cells cultures were separately dyed with DiI or DiO. VYBRANT™ DiI and DiO (Molecular Probes, Eugene, Oreg.) were put to use in accordance with the manufacturers instructions directly for the marking of the cells in suspension. For this purpose, the PC12 cells were washed in the 15 cm cell culture bowl two times with 1×PBS and incubated for 2 to 5 minutes with 1 ml trypsin at 37° C. 5 ml PC12 cell culture medium was added by pipetting and the cells centrifuged for 5 minutes at 400 rpm/4° C. The supernatant was drawn off and the cell pellet re-suspended in 1 ml 1×PBS. There was mixed in 5 ml VYBRANT™ DiI or DiO "Cell Labelling Solutions" (Molecular Probes, V-22889) and the samples incubated for 20 minutes in the incubator at 37° C. and 10% $CO_2$ with occasional shaking. Then the cells were again centrifuged of (5 minutes at 400 rpm/4° C.). The remainder was disposed of and the cell pellet re-suspended in 3 ml culture medium, heated 37° C. The last two steps were repeated twice. Finally, the DiI or DiO dyed cell pellets were taken up in each case in 1 ml cell culture medium, mixed, diluted to ca. 40 ml with cell culture medium and plated onto cell culture bowls. The analysis under the fluorescence microscope shows that both DiI and also DiO practically completely appear in probably endocyted membranous structures and are hardly detectable at the cell membrane (FIGS. 4d-h). At earlier times after the plating out of the mixed culture there were present cells with exclusively green or red fluorescent signals (FIGS. 4f). As soon as two hours later there were found TNT connected cells which contained both green and also red fluorescent signals (FIG. 4d1). With time, the number of the cells increased as also the number of the exchanged fluorescent structures (FIG. 4h). After 24 to 48 hours there were observed in the cells mostly yellow and few green and red fluorescing structures (FIG. 4h), which points to the fusion of the exchanged green and red membranous structures. The unidirectional exchange of membrane vesicles effected via TNTs could thus be simply quantified by means of "Fluorescence Activated Cell Sorting" (FACS), which is a surprisingly simple, very efficient and quantitive method and thus suitable also for pharmacological serial tests for the investigation of an influencing of TNTs and the cell communication thereby realized.

Example 15

Microscopy Method

1. Cell Passage of PC12 Cells

Cells cultivated on 15 cm cell culture bowls (Nalge Nunc International) were washed two times with 1×PBS, then there was added 1 ml trypsin (Trypsin/EDTA solution, Gibco-BRL), and the cells incubated for about 5 minutes at 37° C. (10% $CO_2$). The cells were taken up in 5 ml cell culture medium (see material) and centrifuged for 5 minutes at 400 rpm(4° C.). The cell pellet was re-suspended in 2 ml cell culture medium and taken up; for cell singularisation was pipetted in and out ca. 80 to 100 times with a narrow glas pipette and diluted in the desired volume cell culture medium. The cells were then coated on PLL (Poly-L-Lysin) LABTEK™ cell culture bowls (Chambered Coverglas 4 well, Nalge Nunc International) plated out in desired density.

2. Visualization of TNTs in the Microscope:

The microscope system consisted of an Olympus IX 70 microscope, a PI piezo-z-steppper (E-662, Physik Instrumente GmbH & Co.), a heater box (Life Imaging Services, Olten, Switzerland), a Polychrome II Monochromator (T.I.L.L. Photonics GmbH, Martinsried, Germany), Dapi/FITC/TRITC F61-020 fluorescence filters (AHF Analysentechnik AG, Tübingen, Germany) and control software TILLIVISION™ von T.I.L.L. Photonics GmbH, Martinsried, Munich. The single colour or multicolour fluorescence videomicroscopy was carried out in accordance with standard methods by means of the described system. The same applies for three-dimensional fluorescence or bright field microscopy. In order to be able to see TNTs there must first be found a correct microscopic plane below the floor of the cell culture vessel. Often, the TNTs ran not horizontally to the cell culture vessel, but possessed a certain inclination angle thereto, through which the TNTs could not be resolved completely in one microscopic plane. The TNT could then only be completely imaged through focus changes or three-dimensional studies. For this purpose there were as a rule produced, beginning from the cell base, 40 images of sequential z-section planes through the cell by means of the Z-stepper. This sequence of images was in part processed with the deconvolution extension of the TILLIVISION™ software and three-dimensionally reconstructed and analysed with a suitable software for three-dimensional analysis (by means of VOXBLAST™, TILLIVISION™ or IPLab software v3.2.2. of Scanalytics Inc., Fairfax, Va.). The convocal microscopy was effected with a Leica SP2 confocal microscope, equipped with a 100×HCX PL APO 100×/1.40 NA oil objective (Leica Microsysteme Vertrieb GmbH, Bensheim, Germany). The two imaging systems employed were equipped with a 37° C. heat regulation device (Live Imaging Services, Olten, Switzerland).

3. Wheat Germ Agglutin Staining of TNTs

The cells grown on the LABTEK™ cell culture bowl were treated on the microscope preheated to 37° C., in 450 ml medium, directly with ca. 1 ml "WGA Alexa Fluor™ 594" (1 mg/ml solution) of Molecular Probes (Eugene, Oreg., W-11262). After ca. 2 to 5 minutes the plasma membranes of the cells were then stained and the background in the medium reduced.

4. Immunocytochemical Method

PC12 cells were, 24 hours after cell passage, cautiously washed two times in 1×PBS and cautiously fixed for 20 minutes in 4% PFA/4% sucrose. Then the cells were carefully incubated for 10 minutes in 50 millimolar $NH_4Cl$. The antibody staining was effected in accordance with standard methods, but attention was thereby paid to a careful handling of the samples. In the staining of the nuclei with 4.6-diamino-2-phenylindol-di-hydrochloride (Dapi) (Molecular Probes, dilution 1: 500) and the actin staining with phalloidin, the dyes were so used as if they were antibodies. F-actin was fluorescence marked with phalloidin TRITC/FITC conjugate (Sigma Chemical Co., 250 nanomolar end concentration); see also Rudolf R. et al., *Dynamics of immature secretory granules: role of cytoskeletal elements during transport, cortical restriction and F-actin dependent tethering*, Mol. Biol. Cell, 12, 1353-1365 (2001). The indirect immunofluoresence marking was likewise effected as described in Rudolf R. et al. Further primary antibodies put to use were: polyclonal anti-GFP antibody (Molecular Probes A-6455); monoclonal anti-synaptophysin antibody Sy-38 (Chemicon, Temecula, Calif., dilution 1:100); polyclonal anti-myosin-Va-antiserum-Dil2 (dilution 1:300), of Wu X. et al., *Myosin V associates with melanosomes in mouse melanocytes: evidence that myosin V is an organelle motor.*, J. Cell Sci. 110, 847-859 (1997); monoclonal anti-alpha-tubulin antibody (Klon DM1A, Sigma Chemical Co., dilution 1:500). As secondary antibody there was put to use: goat-anti-mouse-lissamin (dilution 1:500), goat-anti-rabbit-TRITC (dilution 1:200) and goat-anti-rabbit-Cy5 (dilution 1:500), all from Jackson Immuno Research Labs, Inc. (West Grove, Pa.).

5. LABTEK™ Staining

Before the transfer of the PC12 cells to the microscope the cell culture medium was cautiously exchanged for cell culture medium with 60 nanomolar LABTEK™ Green DND-26 (Molecular Probes, Eugene, Oreg., L-7526). The coloured cells could be directly analysed with the aid of fluorescence microscopy.

6. Transfection of Pc12 Cells

The transfection of cDNAs into PC12 cells was effected as described by us in the literature (Kaether C. et al., *Targetting of green fluorescent protein to neuroendocrine secretory granules: a new tool for real time studies of regulated protein secretion*. Eur. J. Cell Biol., 74, 133-142 (1997)).

7. CELLTRACKER™ Staining

The staining was carried out in accordance with the manufacterer'S instructions with adherent cells, i.e. 15 minutes incubation of the cells in medium, which . . . contained, followed by 30 minutes incubation in medium without dye.

Example 16

Method for Testing the Influencing of TNTs

Beyond PC12 cells, TNTs were detected in non-neuroendocrinic HEK-293-cells (ATCC CRL 1573—human embryonic kidney) two days after cell passage (FIG. 16a), medulla primary cultures of the rat (FIG. 16b, for the isolation of the singularised cells, the suprarenal medulla of P10 rats was subject to treatment with collagenase (0.1%) and repeated trypsin treatments (0.125%); the singularised cells were then plated out on polyornithin/laminin coated LABTEK™ cell culture bowls and cultivated for 4 days) and hippocampal primary cultures (FIG. 16c, prepared according to standard methods (Banker, G. Goslin, K. in *Culturing Nerve Cells*, eds. Banker G & Goslin K, MIT Press, Cambridge Mass., 1991)) after colouring with WGA by means of high resolution, three-dimensional video microscopy images (in accordance with Example 15). The morphology and the number of the TNTs formed in these cultures could be determined by means of a three dimensional microscopy analysis in accordance with Example 13. Thus, these or similar cell cultures in combination with the analysis method in Example 13 provide screening systems for testing the influencing of TNTs by means of e.g. cytopharmaceuticals or external energy forms.

1. Screening of Cytopharmaceuticals for Influencing of TNTs

In order to investigate the influence of e.g. cholesterol on the stability of TNTs the cell culture medium of PC12 cells was exchanged, 2 hours after passage, for DMEM with 5.8 or 10 millimolar saccharose (controls) or DMEM with 5, 8 or 10 mM methyl-β-cyclodextrin, and the cells incubated for a half hour at 347° C. and 10% $CO_2$. After addition of WGA there was carried out a three-dimensional analysis of 10 randomly selected microscopy fields (Olympus IX70, 100× objective, TILLIVISION™ System, piezo-z-stepper, in each case 40 sections) and the number of TNTs determined. FIG. 18a1 and FIG. 18b1 show for the 5 millimolar methyl-β-cyclodextrin conditions representative image planes of the three-dimensional analysis, in which TNTs are marked with arrow tips. The quantification revealed a strong reduction of the TNT number with increasing methyl-β-cyclodextrin concentration: ca. 40% reduction with 5 millimolar methyl-β-cyclodextrin; 93% reduction with 8 millimolar methyl-β-cyclodextrin; 100% with 10 millimolar methyl-β-cyclodextrin (FIG. 18c1). In order to detect the effect of methyl-β-cyclodextrin in reducing the cellular cholesterol content there was carried out a filipin staining (Sigma, F-9765) of the cells. For this purpose, the methyl-β-cyclodextrin containing or saccharose containing DMEM of the analysed cells was replaced by DMEM with 20 mg/ml filipin and 15 minutes later the intensity of the fluorescence colouring analysed in vivo with a FITC/TRITC/DAPI filter set (Chroma, Brattleboro). In detail after excitation with 400 nm, four randomly chosen microscopic fields were imaged and the mean grey scale values determined. The evaluation after treatment with 5 millimolar methyl-β-cyclodextrin yielded a reduction of the cellular cholesterol content by 20% (FIG. 18c2). In accordance with this example other cytopharmacological substances can also be tested with regard to an influence of TNTs and the cellular communication depended thereon.

2. Screening of External Wave-like Energy Forms

In the PC12 cell line, TNTs were detected after staining with WGA by means of high resolution three-dimensional videomicroscopy imaging ca. 24 hours after cell passage (FIGS. 1a-d). The influence of external energy forms such as e.g. visible light of a microscope system in accordance with Example 15 Point 2, having a wavelength of 565 nm, was tested on these cells. Over an observation time period of ca. 70 seconds, in which the connection (FIG. 9a) was initially set into oscillation by the incident light of wavelength 565 nm (FIG. 9b), tears (FIG. 9c) and within seconds winds up (FIG. 9d) at its loose end like a torn rubber band. With this model system also influences of other wave-like energy forms on the TNTs can be analysed and the most effective and selective frequencies and intensities of the energy forms employed determined for e.g. therapeutic uses.

Example 17

Principle of Membrane Continuity Between Animal Cells

TNTs form a membrane continuum between the connected cells. Further, TNTs probably represent a new and general cellular principle. This is supposition is supported inter alia by experiments which demonstrate the transfer of plasma membrane components (FIGS. 3n-q2, FIGS. 4a-c) and actin (FIGS. 3j-m2) and the direct transfer of DiI organelles (FIGS. 4d, e, FIG. 14) between TNT connected cells. A comparable membrane continuum is realized in plant organisms by means of plasmodesmata between the cells. With animal organisms, de novo formation of a membrane continuum between cells has not been described. The present view is that as a rule animal cells represent individuals. The model proposed here, TNT mediated membrane continuity between animal cells, together with the discovered transport processes (FIG. 5) therewith allows in principle the exchange of the most varied endogenous or exogenous components between the connected cells. Important components coming into question for such an exchange are e.g. morphogenes or transcription factors which have essential significance for the development or maintenance of the organism. Via the possibilities illustrated in Example 16 of influencing TNTs there are provided wide ranging possibilities to purposively and finely regulatedly influence many and varied biological mechanisms.

The invention claimed is:

1. A method investigating intercellular communication and intercellular transport, comprising:
    singularizing mammalian cells;
    monitoring the singularized mammalian cells for the formation of de novo membrane tubes which contain F-actin and myosin, have a diameter of 50 to 400 nm, and are up to 50 micrometers long,
    wherein said membrane tubes span between the singularized mammalian cells; then
    adding to or expressing in a first population of said cells one or more substances,
    wherein the substance is endocytosed by the cells of the first population or expressed constitutively or transiently by the cells of the first population within a first time period;
    washing said first population of cells;
    mixing the first number of cells with a second population of cells, so that within a second time period intercellular membrane tubes are formed between the cells of the first and second populations, and
    determining the number of cells of the second population of cells which contain the one or more endocytosed or expressed substances.

2. The method according to claim 1, further comprising monitoring organelle transport between the singularized mammalian cells.

3. The method according to claim 1, further comprising prior to mixing the first and second populations of cells, adding to or expressing in the second population of cells one or more substances, wherein the substance is endocytosed by the cells of the second population or expressed constitutively or transiently by the cells of the second population;
    washing the first and second populations of cells;
    mixing the first and second populations of cells so that within a second time period intercellular membrane tubes are formed between the cells of the first and second populations; and determining the number of cells of the first population of cells which contain the one or more endocytosed or expressed substances from the second population of cells, and the number of cells of the second population of cells which contain the one or more endocytosed or expressed substances from the first population of cells, wherein the substances added to or expressed in the first and second populations of cells are different.

4. The method according to claim 1, wherein the one or more endocytosable or expressed substances are selected from one or more of the group consisting of: dyes, fluorescence dyes, Dil, DiO, Lysotracker™, radioactive marker substances, luminescence dyes, fluorescing proteins, luminescing proteins, fluorescing peptides, luminescing peptides, proteins coupled with a marker substance, and peptides coupled with a marker substance.

5. The method according to claim 1, wherein the substance is constitutively or transiently expressed in an organelle.

6. The method according to claim 1, wherein step (iv) further comprises sorting by fluorescence activated cell sorting.

7. The method according to claim 1, wherein a test medium is present in the step of mixing the first population of cells with the second population of cells.

8. The method according to claim 7, wherein the test medium comprises a chemical compound or suspected pharmaceutically effective substance to be tested for activity in affecting organelle transport.

9. The method according to claim 7, wherein the test medium comprises a medicament or therapeutic substance.

10. The method according to claim 1, wherein monitoring comprises observing the singularized mammalian cells with a microscope system, which allows observation of different microscopic planes in a z-axis.

11. The method according to claim 10, wherein the microscope includes a Z-stepper and an associated controller.

12. The method according to claim 7, wherein the test medium is exposed to an energy form to be tested for activity in affecting organelle transport,
wherein the energy form is selected from the group consisting of sound, vibration, heat, hydromechanical energy, and electromagnetic waves.

13. The method according to claim 12, wherein the electromagnetic waves are light waves.

14. The method according to claim 1, wherein the singularized mammalian cells comprise membrane tubes, which contain F actin and myosin Va.

* * * * *